US010913963B2

(12) United States Patent
Carder et al.

(10) Patent No.: US 10,913,963 B2
(45) Date of Patent: Feb. 9, 2021

(54) METHOD AND APPARATUS FOR CONTROLLED HYDROLYSIS

(71) Applicant: The Quaker Oats Company, Chicago, IL (US)

(72) Inventors: Gary Carder, Barrington Hills, IL (US); Yongsoo Chung, Lake in the Hills, IL (US); Prashant Mehta, Chicago, IL (US); Wesley Twombly, Fox River Grove, IL (US)

(73) Assignee: The Quaker Oats Company, Chicago, IL (US)

( * ) Notice: Subject to any disclaimer, the term of this patent is extended or adjusted under 35 U.S.C. 154(b) by 201 days.

(21) Appl. No.: 16/383,430

(22) Filed: Apr. 12, 2019

(65) Prior Publication Data

US 2019/0233864 A1    Aug. 1, 2019

Related U.S. Application Data

(63) Continuation of application No. 15/077,676, filed on Mar. 22, 2016, now abandoned.

(51) Int. Cl.
*C12P 19/14* (2006.01)
*C12M 1/40* (2006.01)
(Continued)

(52) U.S. Cl.
CPC ............. *C12P 19/14* (2013.01); *C12M 21/18* (2013.01); *C12M 45/09* (2013.01); *C12N 9/99* (2013.01); *C12P 19/02* (2013.01); *C12P 21/06* (2013.01)

(58) Field of Classification Search
CPC ................................ C12M 45/09; C12P 19/14
See application file for complete search history.

(56) References Cited

U.S. PATENT DOCUMENTS 1,163,175 A    12/1915   Rullman
1,384,894 A    7/1921    Horlick
(Continued)

FOREIGN PATENT DOCUMENTS

AU    4591389    6/1990
CA    1045890    1/1979
(Continued)

OTHER PUBLICATIONS

Kunert, Joachim, et al., (1999): "On the Triangle Test with Replication," Technical Report, No. 1999, 10 University of Dortmund, 18 Pages.

(Continued)

*Primary Examiner* — Jonathan M Hurst
(74) *Attorney, Agent, or Firm* — Barnes & Thornburg LLP; G. Peter Nichols

(57) ABSTRACT

A method and apparatus for controlled hydrolysis. The method can comprise hydrolyzing a first reagent in a first hydrolysis reaction and deactivating a first enzyme catalyzing the first hydrolysis reaction. The deactivating step can occur in about 10 seconds or less; the deactivating step can comprise adding a deactivating fluid to a composition comprising the first enzyme and heating the first enzyme using a deactivating mechanism. In other aspects, hydrolyzing the first reagent and deactivating the first enzyme can occur in a conduit, and the first hydrolysis reaction can occur in a composition that is at least 50% water by weight. The apparatus can provide a hydrolysis reactor comprising: a conduit; a composition inlet in the conduit for a composition; a first enzyme inlet in the conduit downstream of the composition inlet; and a first deactivating mechanism downstream of the first enzyme inlet to deactivate the first enzyme.

15 Claims, 10 Drawing Sheets

(51) Int. Cl.
*C12P 21/06* (2006.01)
*C12P 19/02* (2006.01)
*C12M 1/00* (2006.01)
*C12N 9/99* (2006.01)

(56) References Cited

U.S. PATENT DOCUMENTS

| | | |
|---|---|---|
| 2,999,018 A | 9/1961 | Huffman et al. |
| 3,116,150 A | 12/1963 | Baker |
| 3,317,402 A | 5/1967 | Smith et al. |
| 3,391,003 A | 7/1968 | Moffatt et al. |
| 3,398,204 A | 8/1968 | Gallant |
| 3,494,769 A | 2/1970 | Tressler |
| 3,579,352 A | 5/1971 | Bookwalter et al. |
| 3,595,671 A | 7/1971 | Cooke et al. |
| 3,732,109 A | 5/1973 | Poat et al. |
| 3,753,728 A | 8/1973 | Bedenk et al. |
| 3,851,085 A | 11/1974 | Rodgers et al. |
| 3,869,558 A | 3/1975 | Hampton et al. |
| 3,925,343 A | 12/1975 | Hampton et al. |
| 3,950,543 A | 4/1976 | Buffa et al. |
| 3,958,016 A | 5/1976 | Galle et al. |
| 4,028,468 A | 6/1977 | Hohner et al. |
| 4,038,427 A | 7/1977 | Martin |
| 4,041,187 A | 8/1977 | Nelson et al. |
| 4,167,584 A | 9/1979 | Nelson |
| 4,171,384 A | 10/1979 | Chwalek et al. |
| 4,247,561 A | 1/1981 | Nelson |
| 4,259,358 A | 3/1981 | Duthie |
| 4,266,027 A | 5/1981 | Muller et al. |
| 4,282,319 A | 8/1981 | Conrad |
| 4,330,625 A | 5/1982 | Miller et al. |
| 4,377,602 A | 3/1983 | Conrad |
| 4,431,674 A | 2/1984 | Fulger et al. |
| 4,435,426 A | 3/1984 | Demame |
| 4,435,430 A | 3/1984 | Fulger et al. |
| 4,438,150 A | 3/1984 | Gantwerker et al. |
| 4,439,460 A | 3/1984 | Tsau et al. |
| 4,500,558 A | 2/1985 | Fulger et al. |
| 4,551,347 A | 11/1985 | Karwowski |
| 4,613,507 A | 9/1986 | Fulger et al. |
| 4,656,040 A | 4/1987 | Fulger et al. |
| 4,668,519 A | 5/1987 | Dartey et al. |
| 4,692,340 A | 9/1987 | Grutte et al. |
| 4,710,386 A | 12/1987 | Fulger et al. |
| 4,777,056 A | 10/1988 | Buhler et al. |
| 4,814,172 A | 3/1989 | Chavkin et al. |
| 4,834,988 A | 5/1989 | Karwowski et al. |
| 4,864,989 A | 9/1989 | Markley |
| 4,886,665 A | 12/1989 | Kovacs |
| 4,894,242 A | 1/1990 | Mitchell et al. |
| 4,996,063 A | 2/1991 | Inglett |
| 4,999,208 A | 3/1991 | Lengerich et al. |
| 4,999,298 A | 3/1991 | Wolfe et al. |
| 5,021,248 A | 6/1991 | Stark et al. |
| 5,045,328 A | 9/1991 | Lewis et al. |
| 5,106,343 A | 4/1992 | Sakaguchi et al. |
| 5,106,634 A | 4/1992 | Thacker et al. |
| 5,145,698 A | 9/1992 | Cajigas |
| 5,234,704 A | 8/1993 | Devine et al. |
| 5,320,856 A | 6/1994 | Veronesi et al. |
| 5,334,407 A | 8/1994 | Donnelly |
| 5,346,890 A | 9/1994 | Hagiwara et al. |
| 5,385,746 A | 1/1995 | De Almeida |
| 5,395,623 A | 3/1995 | Kovach |
| 5,407,694 A | 4/1995 | Devine et al. |
| 5,458,893 A | 10/1995 | Smith |
| 5,464,760 A | 10/1995 | Smith |
| 5,476,675 A | 12/1995 | Lou et al. |
| 5,490,997 A | 2/1996 | Devine et al. |
| 5,523,109 A | 6/1996 | Hellweg |
| 5,554,402 A | 9/1996 | Smith et al. |
| 5,571,334 A | 11/1996 | Dunn et al. |
| 5,593,503 A | 1/1997 | Shi et al. |
| 5,656,317 A | 8/1997 | Smits et al. |
| 5,686,123 A | 11/1997 | Lindahl et al. |
| 5,744,187 A | 4/1998 | Gaynor |
| 5,846,786 A | 12/1998 | Senkeleski et al. |
| 5,849,090 A | 12/1998 | Haralampu et al. |
| 5,863,590 A | 1/1999 | Alan et al. |
| 5,888,548 A | 3/1999 | Wongsuragrai et al. |
| 5,912,031 A | 6/1999 | Fitchett et al. |
| 5,932,264 A | 8/1999 | Hurd et al. |
| 5,962,047 A | 10/1999 | Gross et al. |
| 5,981,237 A | 11/1999 | Meagher et al. |
| 5,985,339 A | 11/1999 | Kamarei |
| 5,997,917 A | 12/1999 | Uchida et al. |
| 6,013,289 A | 1/2000 | Blank et al. |
| 6,054,302 A | 4/2000 | Shi et al. |
| 6,120,722 A | 9/2000 | Schad |
| 6,135,015 A | 10/2000 | Mendez |
| 6,168,821 B1 | 1/2001 | Castleberry |
| 6,190,708 B1 | 2/2001 | Triantafyllou |
| 6,210,738 B1 | 4/2001 | Chen |
| 6,210,741 B1 | 4/2001 | Lengerich |
| 6,221,406 B1 | 4/2001 | Meschonat et al. |
| 6,244,528 B1 | 6/2001 | Wallis et al. |
| 6,257,626 B1 | 7/2001 | Campau |
| 6,277,186 B1 | 8/2001 | Shi et al. |
| 6,287,621 B1 | 9/2001 | Lacourse et al. |
| 6,387,435 B1 | 5/2002 | Fox |
| 6,395,314 B1 | 5/2002 | Whalen et al. |
| 6,420,022 B2 | 7/2002 | Bonke et al. |
| 6,451,369 B1 | 9/2002 | Triantafyllou |
| 6,468,355 B1 | 10/2002 | Thompson et al. |
| 6,485,575 B2 | 11/2002 | Yuan |
| 6,551,366 B1 | 4/2003 | D'Souza et al. |
| 6,592,914 B1 | 7/2003 | Triantafyllou |
| 6,610,349 B1 | 8/2003 | Delrue et al. |
| 6,617,446 B1 | 9/2003 | Papadopoulos et al. |
| 6,685,974 B2 | 2/2004 | Whalen |
| 6,723,358 B1 | 4/2004 | van Lengerich |
| 6,737,099 B2 | 5/2004 | Guraya |
| 6,759,077 B1 | 7/2004 | Lewis et al. |
| 6,797,307 B2 | 9/2004 | Malkki et al. |
| 7,030,092 B1 | 4/2006 | Levine |
| 7,037,704 B2 | 5/2006 | Dunn-Coleman et al. |
| 7,101,585 B2 | 9/2006 | Shen et al. |
| 7,160,564 B2 | 1/2007 | Triantafyllou Oste et al. |
| 7,244,457 B2 | 7/2007 | Racicot et al. |
| 7,318,519 B2 | 1/2008 | Sorensen |
| 7,419,694 B2 | 9/2008 | Korolchuk |
| 7,754,270 B2 | 7/2010 | Wuersch et al. |
| 7,794,774 B2 | 9/2010 | Foster et al. |
| 8,216,363 B2 | 7/2012 | Myerson et al. |
| 8,241,696 B2 | 8/2012 | Chung et al. |
| 8,518,469 B2 | 8/2013 | MacDonald et al. |
| 8,574,644 B2 | 11/2013 | Chatel et al. |
| 8,591,970 B2 | 11/2013 | Chatel et al. |
| 9,149,060 B2 | 10/2015 | Chatel et al. |
| 9,150,895 B2 | 10/2015 | Kurihara et al. |
| 2001/0002269 A1 | 5/2001 | Zhao |
| 2001/0022986 A1 | 9/2001 | Girsh |
| 2002/0127319 A1 | 9/2002 | Gare |
| 2002/0187224 A1 | 12/2002 | Haefliger et al. |
| 2003/0091716 A1 | 5/2003 | Kuramoton et al. |
| 2003/0124195 A1 | 7/2003 | Delprato et al. |
| 2003/0170362 A1 | 9/2003 | Manning et al. |
| 2004/0028797 A1 | 2/2004 | Squire et al. |
| 2004/0101935 A1 | 5/2004 | Vasanthan et al. |
| 2004/0140584 A1 | 7/2004 | Wang et al. |
| 2004/0151805 A1 | 8/2004 | Gao et al. |
| 2004/0219261 A1 | 11/2004 | Triantafyllou Oste et al. |
| 2004/0258829 A1 | 12/2004 | Zheng et al. |
| 2005/0064080 A1 | 3/2005 | Creighton et al. |
| 2005/0089602 A1 | 4/2005 | Kvist et al. |
| 2005/0106216 A1 | 5/2005 | Maurer et al. |
| 2005/0181114 A1 | 8/2005 | Bruemmer |
| 2005/0191400 A1 | 9/2005 | Satyavolu et al. |
| 2005/0214347 A1 | 9/2005 | Astrup et al. |
| 2005/0233051 A1 | 10/2005 | Shen |
| 2005/0238777 A1 | 10/2005 | Klingeberg et al. |
| 2005/0244563 A1 | 11/2005 | Cavalieri et al. |
| 2005/0260305 A1 | 11/2005 | Adele et al. |

(56) References Cited

U.S. PATENT DOCUMENTS

| | | |
|---|---|---|
| 2006/0008574 A1 | 1/2006 | Begli et al. |
| 2006/0013940 A1 | 1/2006 | Mueller et al. |
| 2006/0093720 A1 | 5/2006 | Tatz |
| 2006/0115573 A1 | 6/2006 | Singer et al. |
| 2006/0121174 A1 | 6/2006 | Franke |
| 2006/0134299 A1 | 6/2006 | Lahteenmaki |
| 2006/0141097 A1 | 6/2006 | Guo |
| 2006/0240148 A1 | 10/2006 | Nguyen et al. |
| 2006/0251791 A1 | 11/2006 | Rubio et al. |
| 2006/0257548 A1 | 11/2006 | Crofskey et al. |
| 2006/0280838 A1 | 12/2006 | Kvist et al. |
| 2006/0286269 A1 | 12/2006 | Shah et al. |
| 2007/0014892 A1 | 1/2007 | Mitchell et al. |
| 2007/0026105 A1 | 2/2007 | Seo et al. |
| 2007/0059340 A1 | 3/2007 | Bello et al. |
| 2007/0071857 A1 | 3/2007 | Vemuganti |
| 2007/0141218 A1 | 6/2007 | Chatel et al. |
| 2007/0154609 A1 | 7/2007 | Li et al. |
| 2007/0172568 A1 | 7/2007 | Spelman |
| 2007/0178199 A1 | 8/2007 | Minor et al. |
| 2007/0184175 A1 | 8/2007 | Rubio et al. |
| 2007/0212472 A1 | 9/2007 | Holenstein |
| 2007/0243301 A1 | 10/2007 | Barnett et al. |
| 2007/0264400 A1 | 11/2007 | Milne et al. |
| 2007/0292583 A1 | 12/2007 | Haynes et al. |
| 2008/0003340 A1 | 1/2008 | Karwowski et al. |
| 2008/0008801 A1 | 1/2008 | Barnekow et al. |
| 2008/0098900 A1 | 5/2008 | Aremu et al. |
| 2008/0131582 A1 | 6/2008 | Karwowski et al. |
| 2008/0171114 A1 | 7/2008 | Bernardino et al. |
| 2008/0260909 A1 | 10/2008 | Chung et al. |
| 2008/0305212 A1 | 12/2008 | Wong et al. |
| 2009/0053771 A1 | 2/2009 | Dale et al. |
| 2009/0148562 A1 | 6/2009 | Lin et al. |
| 2009/0181128 A1 | 7/2009 | Blumenthal et al. |
| 2009/0221041 A1 | 9/2009 | Aux |
| 2009/0253191 A1 | 10/2009 | Ward |
| 2009/0311376 A1 | 12/2009 | Rao et al. |
| 2010/0015306 A1 | 1/2010 | Pereyra |
| 2010/0104718 A1 | 4/2010 | Durand et al. |
| 2010/0112127 A1 | 5/2010 | Chatel et al. |
| 2010/0112167 A1 | 5/2010 | Chatel et al. |
| 2010/0178400 A1 | 7/2010 | Pereyra et al. |
| 2010/0189870 A1 | 7/2010 | Frohberg et al. |
| 2010/0316765 A1 | 12/2010 | French et al. |
| 2011/0020523 A1 | 1/2011 | Pereyra et al. |
| 2012/0082740 A1 | 4/2012 | Collins et al. |
| 2012/0245111 A1 | 9/2012 | Hoebler |
| 2013/0017300 A1 | 1/2013 | Avila et al. |
| 2013/0170362 A1 | 7/2013 | Futak |
| 2013/0183405 A1 | 7/2013 | Chatel et al. |
| 2013/0209610 A1 | 8/2013 | Carder et al. |
| 2013/0323799 A1 | 12/2013 | Takaha et al. |
| 2014/0017356 A1 | 1/2014 | Biesebeke et al. |
| 2014/0050819 A1 | 2/2014 | Chatel et al. |
| 2014/0087430 A1 | 3/2014 | Lee et al. |
| 2014/0170723 A1 | 6/2014 | Dobson et al. |
| 2014/0193563 A1 | 7/2014 | Carder et al. |
| 2014/0193564 A1 | 7/2014 | Carder et al. |
| 2015/0183821 A1 | 7/2015 | Konstantinov et al. |
| 2015/0191758 A1 | 7/2015 | Larsen et al. |
| 2015/0351432 A1 | 12/2015 | Triantafyllou |
| 2016/0185641 A1 | 6/2016 | Zuback |

FOREIGN PATENT DOCUMENTS

| | | |
|---|---|---|
| CA | 2015149 | 10/1990 |
| CN | 1386446 | 12/2002 |
| DE | 970141 | 8/1958 |
| EP | 0078782 | 5/1983 |
| EP | 0231729 | 8/1987 |
| EP | 0312220 | 4/1989 |
| EP | 0474230 | 3/1992 |
| EP | 0512249 | 11/1992 |
| EP | 0634106 | 1/1995 |
| EP | 1723853 | 11/2006 |
| EP | 1782697 | 5/2007 |
| EP | 1872666 | 1/2008 |
| FR | 2620906 | 3/1989 |
| GB | 1168692 | 10/1969 |
| JP | S63116657 | 5/1988 |
| JP | 2000004852 | 1/2000 |
| JP | 2002171920 | 6/2002 |
| JP | 2009207359 | 9/2009 |
| JP | 2010051285 | 3/2010 |
| RU | 2044503 | 9/1995 |
| RU | 2237419 | 7/2004 |
| WO | 9210106 | 6/1992 |
| WO | 1993000826 | 1/1993 |
| WO | 9413826 | 6/1994 |
| WO | 9604799 | 2/1996 |
| WO | 2000030457 | 6/2000 |
| WO | 2009127687 | 6/2000 |
| WO | 2003011052 | 2/2003 |
| WO | 2003090557 | 11/2003 |
| WO | 2006009169 | 1/2006 |
| WO | 2007020059 | 2/2007 |
| WO | 2008028994 | 3/2008 |
| WO | 2008096044 | 8/2008 |
| WO | 2008097619 | 8/2008 |
| WO | 2008097620 | 8/2008 |
| WO | 2009077659 | 6/2009 |
| WO | 2009109703 | 9/2009 |
| WO | 2009158588 | 12/2009 |
| WO | 2014160351 | 10/2014 |

OTHER PUBLICATIONS

Watts, et al., "Basic Sensory Methods for Food Evaluation." International Development Research Centre, 1989, 164 pages.

Skoglund, M., "Avenanthramide Content and Related Enzyme Activities in Oats as Affected by Steeping Germination," Journal of Cereal Science, Academic Press Ltd, GB, vol. 48, No. 2, Sep. 1, 2008, pp. 294-303, XP023979477, 10 pages.

Berger, R.G., "Flavours and Fragrances—Chemistry, Bioprocessing and Sustainability," Springer-Verlag Berlin Heidelberg, 2007, p. 464, p. 483 (20 pages).

Howling, D., "Mechanisms of Starch Enzymolysis," International Biodeterioration 25, 1989, p. 1989, p. 15-19 (5 pages).

Jay, James, "Modern Food Microbiology," 7th Edition, p. 123 f., Springer Science+Business Media, Inc. 2005 (23 pages).

Polaina, Julio and MacCabe, Andrew, "Industrial Enzymes—Structure, Function, and Applications" Springer 2007, p. 1-34 (34 pages).

Encyclopedia of Food Sciences and Nutrition, 2003, 2nd ed., searched for "beta-glucan"—https://www.sciencedirect.com/topics/biochemistry-genetics-and-molecular-biology/beta-glucan (visited homepage on Aug. 16, 2018) (2 pages).

Hareland, G.A., "Evaluation of Flour Particle Size Distribution by Laser Diffraction, Sieve Analysis and Near-Infrared Reflectane Spectroscopy," 1994, vol. 20, Issue 2, Abstract (visited homepage on Aug. 17, 2018) (1 page).

Kent, James A., "Kent and Riegel's Handbook of Industrial Chemistry and Biotechnology," Spring Science+Business Media, LLC, 2007, vol. 1, 11th ed., pp. 1684-1685, (6 pages).

Reddy, Avanija, et al., "The pH of beverages in the United States," 2016, vol. 147, Issue 4, pp. 255-263, (10 pages).

Srilakshmi, B., "Food Science," New Age International, 2003, 3rd ed., p. 269, (5 pages).

Camire, Mary Ellen, et al., "Thermal Processing Effects on Dietary Fiber Composition and Hydration Capacity in Corn Meal, and Potato Peels," Cereal Chemistry 68(6), pp. 645-647, No. 6, 1991 (3 pages).

Singh, Narpinder, et al., "A Comparision of Wheat Starch, Whole Wheat Meal and Oat Flour in the Extrusion Cooking Process," J. Food Engineering 34 (1997) 15-32 (18 pages).

Tapola, N., et al. "Glycemic responses of oat brain products in type 2 diabetic patients," Nutrition, Metabolism & Cardiovascular Diseases (2005) 15, 255-261 (7 pages).

(56) References Cited

OTHER PUBLICATIONS

Vasanthan, et al., "Dietary fiber profile of barley flour as affected by extrusion cooking," Food Chemistry 77 (2002) pp. 35-40 (6 pages).
Likimani, T.A., "Extrusion Cooking of Corn/Soybean Mix in Presence of Thermostable a-Amylase," Journal of Food Science, vol. 56, No. 1, 1991, pp. 99-105 (7 pages).
Hao, L.. Food Additives, 1st Edition, p. 246-247, Chine Agricultural University Press, China, Aug. 2002.
Li, Z. et al., "Fermented Food Technology," China Metrology Publishing House, p. 141, 2012.
Zheng, B. "Food Enzymology," Southeast University Press, p. 132, 2006.
Hosney, R. Carl, "Principles of Cereal Science and Technology," 1986, American Association of Cereal Chemists, Inc., St. Paul, Minnesota 55121, pp. 148-149 (4 pages).
Anderson, et al., "Gelatinazation of corn frits by roll cooking, extrusion cooking and steaming." Staerke, 22:130-135.
Anonymous: "Ovsena nahradka mlieka," XP002561727, URL:http://web.archive.org/web/20084200751 51/http://www.aspsk.sk/ovsene_mlieko.htm>, retrieved from the internet on Dec. 18, 2009, pp. 1-1, dated Apr. 20, 2008.
Anonymous: "Goldkill Instant Barley Drink" XP002561728, URL:http:f/web.archive.org/web/20060303003347/goldkill.\l .com/goldkili_instant.php>, retrieved from the Internet on Dec. 28, 2009, pp. 1-2, dated Mar. 3, 2006.
Brenda, The comprehensive Enzyme Information System, BC 3.2.1.1.—alpha amylase; pp. 1 to 297: retrieved from the InternetL http://www.brenda-enzymes.info/php/result_flat.php4?ecno=3.2.1.1 &organism_list=, date unknown.
Changquing, et al., Study on the Extruding Production Method of Soluble Oats Fiber, vol. 28, No. 2, pp. 45-48, dated Mar. 20, 2002, with English Abstract.
Grenus, Food Product Design, Applications, Agglomerations, Jul. 10, 2014, Weeks Publishing Co., pp. 1-4, www.foodproductdesign.com/articles/2004/07/food-product-design-applications.
Gualberto, D.G. et al, Effect and extrusion processing on the soluble and insoluble fiber, and phytic acid contents of cereal brans, dated Sep. 28, 1997.
Gutkoski, L.C., et al., Effect of Extrusion Process Variables on Physical and Chemical Properties of Extruded Oat Products, Plant Foods for Human Nutrition, 200.
Inglett, G.E. et al., Oat beta-glucan-amylodextrin: Preliminary preparations and biological properties, plant Fd. For Human Nutrition, vol. 45, pp. 53-61, dated Jun. 5, 2012.
Linko Y Y et al., The effect of HTST-extrusion on retention of cereal alpha-amylase activity on enzymatic hydrolisis of barley starch, Food Processing Systems, Applied Science Publ, UK, Jan. 1, 1980, pp. Abstr, 4.2.25, 210-223, XP009127925, ISBN: 978-0-85334-896-2.
PCT Application No. PCT/US2008/060323 International Search Report dated Aug. 13, 2008.
PCT Application No. PCT/US2009/060016 International Search Report dated Apr. 8, 2010.
PCT Application No. PCT/US2009/060016, International Preliminary Report on Patentability dated May 19, 2011.
PCT Application No. PCT/US2009/059916 International Search Report and Written Opinion dated Apr. 16, 2010.
PCT Application No. PCT/US2014/21913 International Search Report and Written Opinion dated Jun. 23, 2014.
PCT Application No. PCT/US2010/038506 International Search Report and Written Opinion dated Aug. 10, 2010.
PCT Application No. PCT/US2014/17288 International Search Report and Written Opinion dated Jun. 13, 2014.
PCT Application No. PCT/US2014/26367 International Search Report and Written Opinion dated Sep. 9, 2014.
Peter Koelln KGAA: Kochjule, Hafer-Getrank mit Fruchtsaft, XP002499645, Internet Citation, URL:http://www.koelin.de/downloads/37/Kochjule.pdf>, retrieved from the Internet on Oct. 14, 2008, pp. 1-19.
Peter Kolin KGAA: Kolln Schmetzflocken Dinkel-Hafer, XP002499438, Internet Citation, URL:http:f/www.koelln.de/produkte/2/103/index.html>, retrieved from the Internet on Oct. 13, 2008, p. 1.
Peter Kolin KGAA: KollnFlocken Instant, XP00249937, Internet Citation, URL:http:f/www.koelln.de/produckte/1/15/index.html>, retrieved from the Internet on Oct. 13, 2008, p. 1.
Vasanthan, et al., Dextrinization of Starch Barley Flurs with Thermostable alpha-Amylase by Extrusion Cooking, vol. 53, No. 12, pp. 616-622, dated Dec. 1, 2001.
Wang, Ming-chun et al., Extrusion Technology Applied in the Nutritional Health Foods, College of Food Engineering & Biologic Technology, Tianjin University of Science and Technology, Tianjin 300457, pp. 63-66, dated Aug. 1, 2007, with English Abstract.
The Whole Grains Council, What are the Health Benefits?, http://wholegrainscouncil.org/whole-grains-101/what-are-the-health-benefits, 2 pages.
Zhang Haodong, "Starch Article Technology," Jilin Science and Technology Press, Apr. 29, 2008.
Davis, "The Effect of Cold on Micro-Organisms in Relation to Dairying," Express Dairy Co (London), Proceedings of the Society for Applied Bacteriology, vol. 14, Issue 2, pp. 216-242, Oct. 1951.
Food Reference, About.com "Why Does Milk Curdle," http://foodreference.about.com/od/Dairy/Why-Does-Milk-Curdle.htm, pp. 1-2.
PCT Application No. PCT/US2012/046450 International Search Report and Written Opinion dated Sep. 6, 2012.
Office action and Search Report dated Jul. 31, 2020 in Russian Application No. 2018135299.

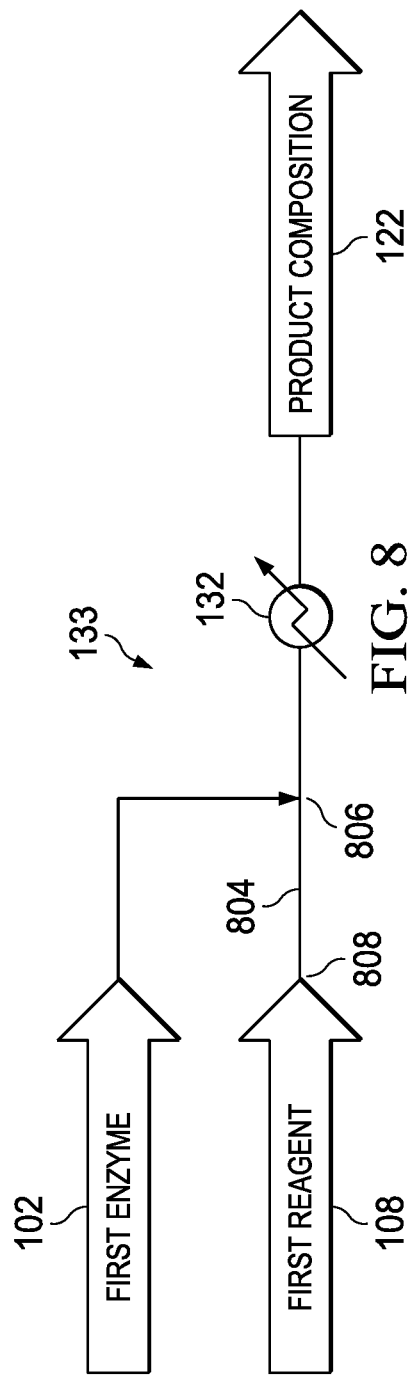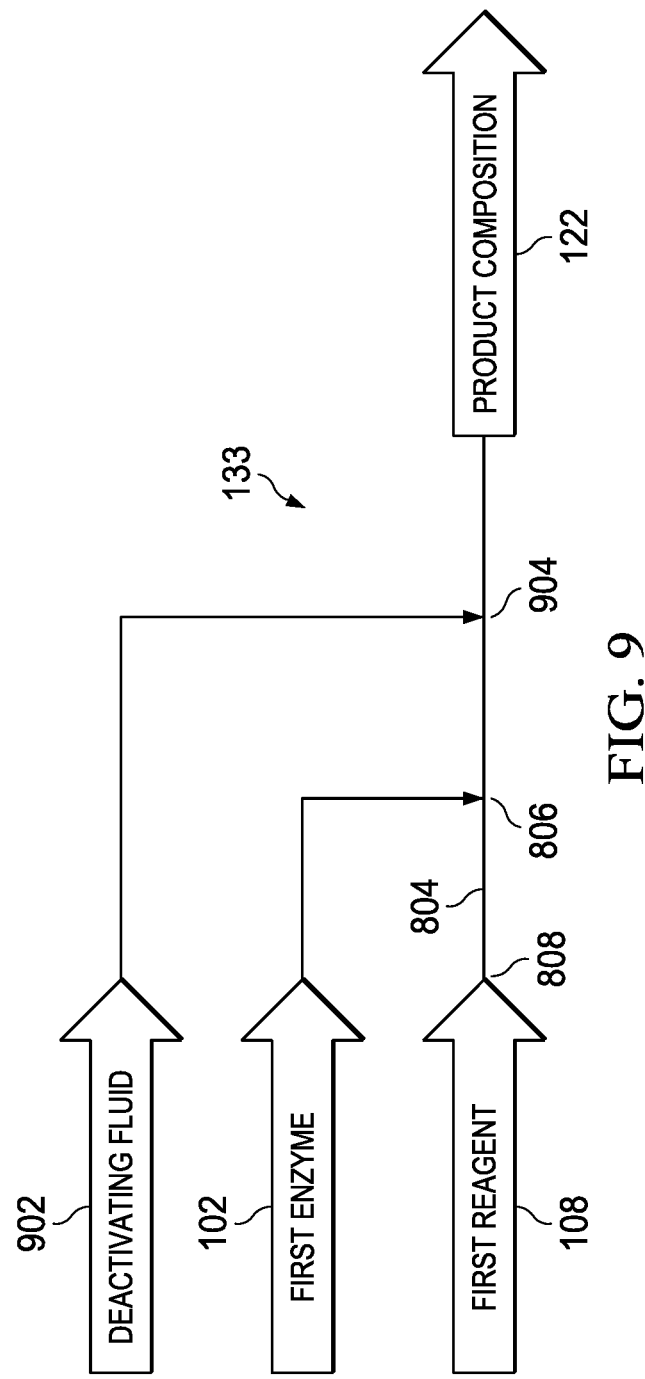

METHOD AND APPARATUS FOR CONTROLLED HYDROLYSIS

CROSS-REFERENCE TO RELATED APPLICATIONS

The present application is a continuation application of and claims priority to U.S. Nonprovisional patent application Ser. No. 15/077,676, entitled "Method and Apparatus for Controlled Hydrolysis," filed on Mar. 22, 2016, and published as U.S. 2017-0275662-A1 on Sep. 28, 2017, which application and publication are herein incorporated by reference in their entirety as examples.

BACKGROUND

Technical Field

The present invention relates to controlling a hydrolysis reaction. For example, in some embodiments, the invention relates to activating and deactivating an enzyme that catalyzes a hydrolysis reaction to start and stop the hydrolysis reaction, respectively. In some embodiments, the invention relates to a starch hydrolysis reaction, fiber hydrolysis reaction, and/or protein hydrolysis reaction. Further, in some embodiments, the invention relates to hydrolysis of relatively-higher-molecular-weight molecules (e.g., protein, starch and/or fiber molecules) in at least a portion of a pulse and/or grain to convert the relatively-higher-molecular-weight molecules into relatively-lower-molecular-weight molecules. Also, in some embodiments, the invention relates to deactivation of a hydrolysis-catalyzing enzyme before the enzyme-catalyzed hydrolysis reaction converts an undesirable amount of starch molecules and/or fiber molecules into monosaccharides or disaccharides.

Background

Existing hydrolysis processes (e.g., for hydrolyzing starch molecules and/or fiber molecules) do not provide a desirable production rate, a desirable degree of control over the extent of hydrolysis, or a continuous (as opposed to batch) process, while also avoiding the use of certain equipment that can raise capital costs.

SUMMARY OF THE INVENTION

In a first aspect, the present invention provides a method comprising the steps of hydrolyzing a first reagent in a first hydrolysis reaction; and deactivating a first enzyme catalyzing the first hydrolysis reaction. The deactivating step lasts no more than about 10 seconds.

In a second aspect, the invention provides a method comprising: hydrolyzing a first reagent in a first hydrolysis reaction; and deactivating a first enzyme catalyzing the first hydrolysis reaction. The deactivating step comprises adding a deactivating fluid to a composition comprising the first enzyme.

In a third aspect, the invention provides a method comprising: hydrolyzing a first reagent in a first hydrolysis reaction; and deactivating a first enzyme catalyzing the first hydrolysis reaction. The deactivating step comprises heating the first enzyme using a deactivating mechanism.

In a fourth aspect, the invention provides a method comprising: hydrolyzing a first reagent in a first hydrolysis reaction; and deactivating a first enzyme catalyzing the first hydrolysis reaction. The hydrolyzing the first reagent and the deactivating the first enzyme occur in a conduit.

In a fifth aspect, the invention provides a method comprising: hydrolyzing a first reagent in a first hydrolysis reaction; and deactivating a first enzyme catalyzing the first hydrolysis reaction. The first hydrolysis reaction occurs in a composition that is at least 50 wt. % water.

In a sixth aspect, the invention provides a hydrolysis reactor comprising: a conduit; a composition inlet in the conduit for a composition; a first enzyme inlet in the conduit downstream of the composition inlet; and a first deactivating mechanism downstream of the first enzyme inlet to deactivate the first enzyme.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 8 is a schematic process flow diagram illustrating one embodiment of the invention that uses a deactivating heater to deactivate an enzyme.

FIG. 9 is a schematic process flow diagram illustrating one embodiment of the invention using a deactivating fluid to deactivate an enzyme.

DETAILED DESCRIPTION

Figure 1:
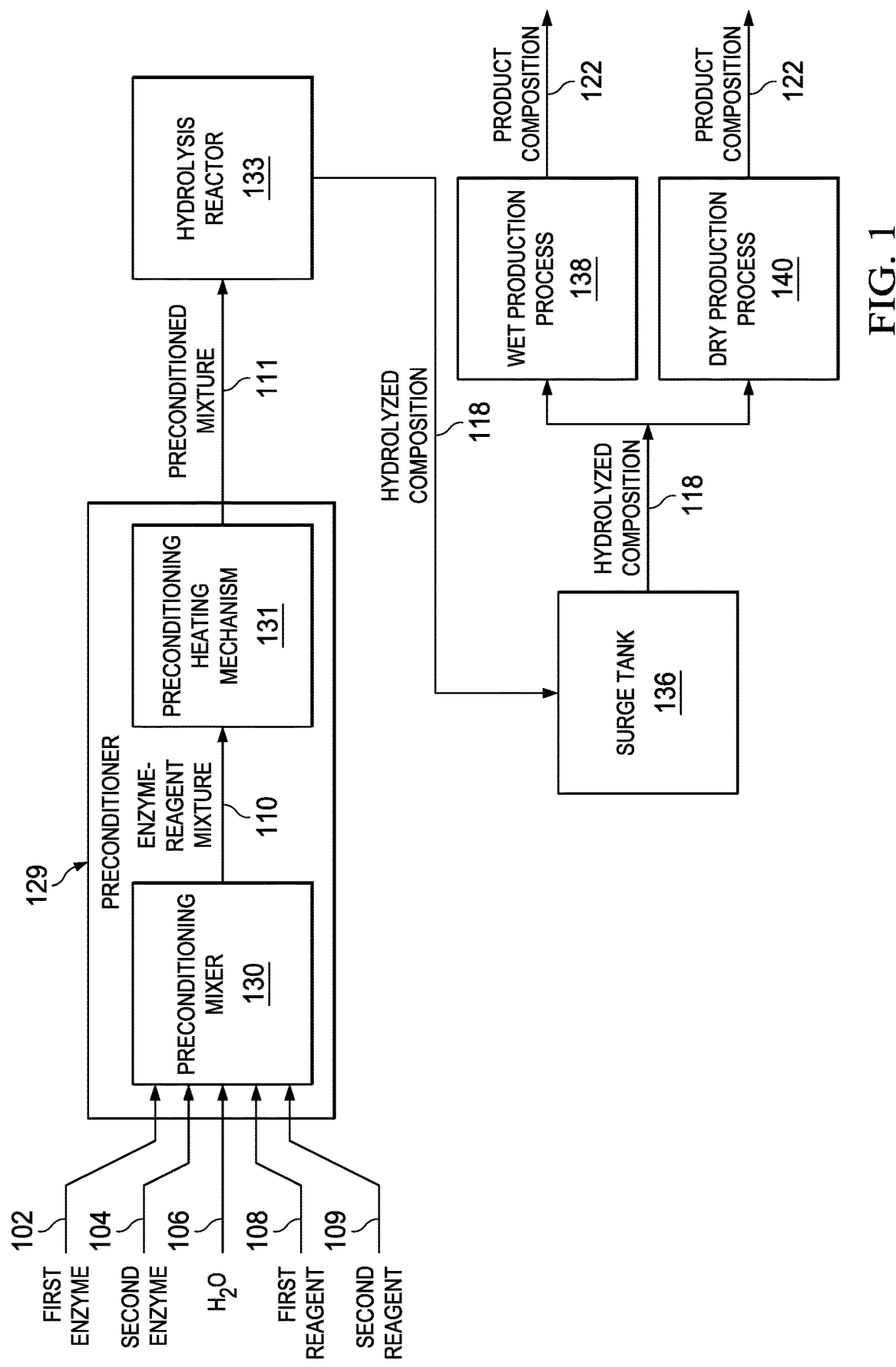
FIG. 1 is a block flow diagram illustrating one embodiment of the invention.

Although the invention described herein has many potential applications, one embodiment provides a desired mass concentration of at least a portion of grain (e.g., whole grain or bran) to a food product, for example a beverage, while avoiding high viscosities and an undesirable mouthfeel that are typically associated with the concentration of at least a portion of grain (e.g., whole grain or bran). In some embodiments, this is achieved by the enzyme-catalyzed hydrolysis of the starch, fiber, and/or protein in a composition comprising the at least a portion of grain. For example, the hydrolysis reaction can be started to reduce the molecular weight of starch, fiber or protein molecules, but the hydrolysis reaction can be stopped before the starch or fiber is converted to monosaccharides or disaccharides or the protein is converted to one or more amino acid molecules.

Moreover, in some embodiments, the average molecular weight of the starch molecules can be reduced to a fraction of the original average molecular weight (e.g., no more than about 60%, 50%, 40%, 30%, 20%, 10%, 9%, 8%, 7%, 6%, 5%, 4%, 3%, 2%, or 1% of the original molecular weight). This is so, because, for example, the starch molecules can be selectively reduced (e.g., using enzymes with only endo activity) in molecular weight to the smallest molecules that still constitute starch, but without being converted into molecules that are not starch, such as sugar (e.g., monosaccharides or disaccharides).

Similarly, in some embodiments, the average molecular weight of the fiber molecules can be reduced (e.g., using enzymes with only endo activity) to a fraction of the original average molecular weight (e.g., no more than about 60%, 50%, 40%, 30%, 20%, 10%, 9%, 8%, 7%, 6%, 5%, 4%, 3%, 2%, or 1% of the original molecular weight). This is so, because, for example, the fiber molecules can be selectively reduced in molecular weight to the smallest molecules that still constitute fiber, but without being converted into molecules that are not fiber, such as sugar (e.g., monosaccharides or disaccharides).

Furthermore, in some embodiments, the average molecular weight of the protein molecules can be reduced (e.g., using enzymes with only endo activity) to a fraction of the original average molecular weight (e.g., no more than about 60%, 50%, 40%, 30%, 20%, 10%, 9%, 8%, 7%, 6%, 5%, 4%, 3%, 2%, or 1% of the original molecular weight). This is so, because, for example, the protein molecules can be selectively reduced in molecular weight to the smallest molecules that still constitute protein, but without being converted into molecules that are not protein, such as individual amino acids. In some embodiments, a desired mass concentration of at least a portion of grain is provided in a wet hydrolysis process, as opposed, for example, to an extruder. Using a wet hydrolysis process (e.g., a vessel filled with water) can be advantageous because such a relatively simple process can avoid the need for more complicated or expensive equipment such as an extruder. However, a wet hydrolysis process can also be difficult to control. For example, an abundance of water in a wet hydrolysis process can result in a quick hydrolysis reaction, and the reaction can quickly produce an undesirable concentration of monosaccharides and disaccharides from starch or fiber, which can destroy whole grain status or other desired characteristics. As an additional example, it can be difficult to control the temperature throughout a large volume of liquid in a large vessel used for batch hydrolysis reactions. This can, in turn, result in different hydrolysis reaction rates in different locations within the liquid. As yet another example, a large volume can make it difficult to deactivate an enzyme that catalyzes hydrolysis after achieving a desired percent conversion from larger starch or fiber molecules to smaller starch or fiber molecules. In practice, this means it can be difficult to control the molecular weight of the hydrolysis products and rather than producing smaller starch and fiber molecules, monosaccharides and disaccharides can be produced.

Advantageously, the inventors have developed a new and useful invention providing a controlled hydrolysis process. For example, some embodiments of the invention provide a continuous process for hydrolyzing a composition comprising starch, fiber, or protein. An example of a composition comprising starch, fiber, or protein is a slurry comprising water and at least a portion of a grain or a pulse.

As another example, in some embodiments, a composition comprising starch, fiber, and/or protein flows through a pipe. At an inlet in the pipe, at least one enzyme enters the pipe and combines with the composition, thereby catalyzing the hydrolysis of the starch, fiber, and/or protein. Then, after a specified period of time has passed, or in order to achieve a target percent conversion of starch, fiber, and/or protein, or in order to achieve a target molecular weight distribution of starch, fiber, and/or protein, the at least one enzyme is deactivated, for example, by heating the enzyme. As an illustration, in some embodiments, the enzyme is heated by injecting steam into the composition comprising the enzyme. The deactivation of the enzyme, in turn, stops the enzyme-catalyzed hydrolysis of the starch, fiber, and/or protein, thereby providing hydrolyzed starch molecules or hydrolyzed fiber molecules with a reduced molecular weight distribution while avoiding the production of monosaccharides and disaccharides or hydrolyzed fiber molecules while avoiding the production of amino acid molecules.

To catalyze fiber hydrolysis, some embodiments use a fibrolytic enzyme (e.g., endo-glucanase). Examples of endo-glucanase include endo-cellulase, which hydrolyzes insoluble fiber (e.g., cellulose) and soluble fiber (e.g., beta-glucan), and endo-beta-glucanase, which hydrolyzes soluble fiber. In some embodiments, it is useful to use substantially pure endo-glucanase (e.g., substantially no α-amylase activity and/or substantially no exo-enzyme activity). In some embodiments, the substantially pure endo-cellulase provides better results in terms of controlled molecular weight reduction because the endo-cellulase can hydrolyze both soluble and insoluble fiber.

To catalyze starch hydrolysis, some embodiments use α-amylase. In some embodiments, it is useful to use substantially pure α-amylase (e.g., substantially no cellulase activity and glucanase activity, and substantially no exo-enzyme activity). The substantially pure α-amylase can provide better results in terms of controlled molecular weight reduction relative to, for example, β-amylase.

In embodiments where the α-amylase has higher molecular weight average and/or distribution is achieved for the lower molecular weight starch.

One embodiment of the invention will now be illustrated with a preconditioned mixture 111. In some embodiments, the preconditioning heater comprises an infrared device, a microwave device, an ultrasonic device, or a heat exchanger (e.g., a heat jacket). Additionally, in some embodiments, the preconditioning mixer 130 and the preconditioning heating mechanism 131 are combined, for example, in a preconditioner 129. Accordingly, in some embodiments mixing the reaction components to provide an enzyme-reagent mixture 110 and heating the enzyme-reagent mixture 110 to provide a preconditioned mixture 111 take place simultaneously in a preconditioning step 302. As used herein, preconditioning means conditioning a composition before hydrolysis, and a preconditioner 129 is a unit that conditions a composition before hydrolysis. To provide some non-exhaustive illustrations, preconditioning (e.g., with a preconditioner 129) can be used to provide a composition with a desired moisture composition, temperature, particle size, viscosity, and/or degree of homogeneity for a hydrolysis reaction. Accordingly, in some embodiments preconditioning can comprise heating and/or mixing, and a preconditioner 129 can comprise a mixer and/or heater.

With reference again to FIG. 1, the preconditioned mixture 111 is fed to a hydrolysis reactor 133 to provide a hydrolyzed composition 118. In some embodiments, the hydrolyzed composition 118 is fed to a surge tank 136, for example, to provide storage for the hydrolyzed composition 118 or to provide more control over the rate at which the hydrolyzed composition 118 is fed to any downstream processes. Furthermore, in some embodiments, the hydrolyzed composition 118 is fed to a wet production process 138 and/or a dry production process 140 to provide a product composition 122.

Although the embodiment is illustrated using a first reagent 108 and a second reagent 109, in some embodiments only the first reagent 108 or only the second reagent 109 are hydrolyzed. For example, in some embodiments, when only the first reagent 108 is hydrolyzed in a first hydrolysis reaction, the first enzyme 102 is used to catalyze the first hydrolysis reaction and the second enzyme 104 is unnecessary and is not used. As another example, in some embodiments, when only the second reagent 109 is hydrolyzed in a second hydrolysis reaction, only the second enzyme 104 is used to catalyze the second hydrolysis reaction.

Additionally, although illustrated separately in the embodiment shown in FIG. 1, in some embodiments a mixer (e.g., in a preconditioner 129) comprises both the preconditioning mixer 130 and the preconditioning heating mechanism 131. Accordingly, in some embodiments, the heating and the mixing occur simultaneously. Furthermore, in some embodiments the order of the preconditioning mixer 130 and the preconditioning heating mechanism 131 are interchanged. Also, in some embodiments, the order of the preconditioning heating and preconditioning mixing are interchanged.

Figure 6:
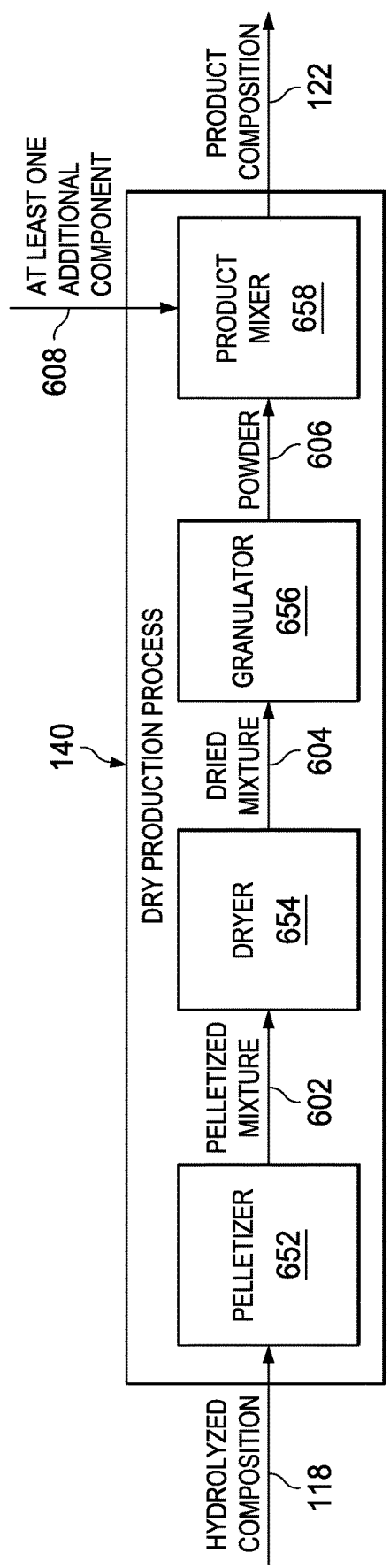
FIG. 6 is a block flow diagram illustrating one embodiment of the invention in which a hydrolyzed composition is fed to a dry production process to produce a product composition.

FIG. 6 illustrates an example of a dry production process 140 for providing a product composition 122. As illustrated in FIG. 6, the dry production process 140 comprises a plurality of steps. First, the hydrolyzed composition 118 is fed to a pelletizer 652 to pelletize the hydrolyzed composition 118 and provide a pelletized mixture 602. Second, the pelletized mixture 602 is fed to a dryer 654 to dry the pelletized product and provide a dried mixture 604. Third, the dried mixture 604 is fed to a granulator 656 to granulate the dried mixture 604 and provide a powder 606. Fourth, the powder 606 and at least one additional component 608 are fed to a product mixer 658 to mix the powder 606 and the at least one additional component 608 and provide a product composition 122. Examples of a product composition 122 from a dry production process 140 include powder 606 or solid food, for example, beverage powder 606, batter, flour, and a baking mix. Although, the product composition 122 can also be added to a liquid-based food such as beverage or a soup.

Although the pelletizing step 218 is one method for preparing the hydrolyzed composition 118 to be dried, the pelletizing step 218 is intended to be a specific example of a physical division step that physically separates the hydrolyzed composition 118 into discrete pieces having approximately the same compositions. Accordingly, herein, a pelletizing step 218 can be replaced with a physical division step, a pelletized mixture 602 can be replaced with a divided mixture, and a pelletizer 652 can be replaced with a divider. Additionally, in any embodiment in which a pelletizing step 218, pelletizer 652, or pelletized mixture 602 is used, the pelletizing step 218, pelletizer 652, or pelletized mixture can be omitted to provide another embodiment. For example, with reference to FIG. 2, FIG. 3, and FIG. 6, a hydrolyzed composition 118 can be dried in a dryer 654 to provide a dried mixture 604 without a pelletizing step 218 before the drying step 220. Accordingly, in some embodiments, a hydrolyzed composition 118 is dried in any form, which can be a pelletized form or some other form.

Figure 7:
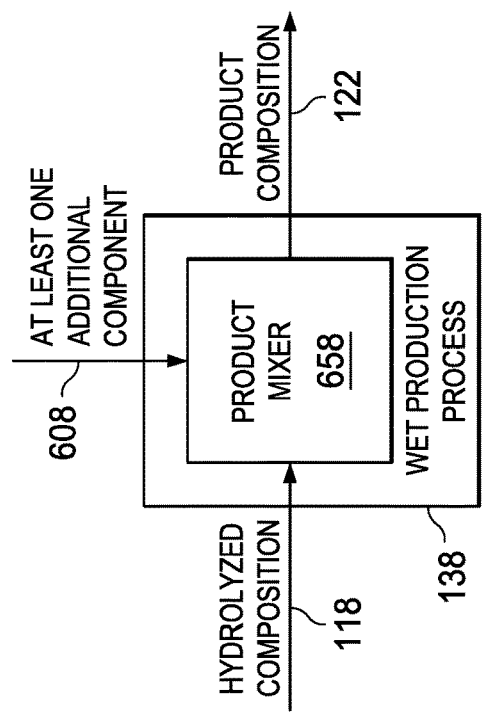
FIG. 7 is a block flow diagram illustrating one embodiment of the invention in which a hydrolyzed composition is fed to a wet production process to produce a product composition.

FIG. 7 illustrates an example of a wet production process 138 for providing a product composition 122. As distinguished from the dry production process 140, the wet production process 138 does not require drying. This can be advantageous because the hydrolyzed composition 118 has a fairly high moisture content (e.g., at least about 50% in some embodiments). As illustrated in FIG. 7, the wet production process 138 is also advantageous because it comprises only a single mixing step, which can be less complicated than a dry production process 140. Nonetheless, where desirable, a wet production process 138 can also comprise additional steps.

In the wet production process 138 illustrated in FIG. 7, a hydrolyzed composition 118 and at least one additional component 608 are fed to a product mixer 658 to mix the hydrolyzed composition 118 and the at least one additional component 608 and provide a product composition 122. Examples of a product composition 122 from a wet production process 138 include beverages and soups.

Figure 4:
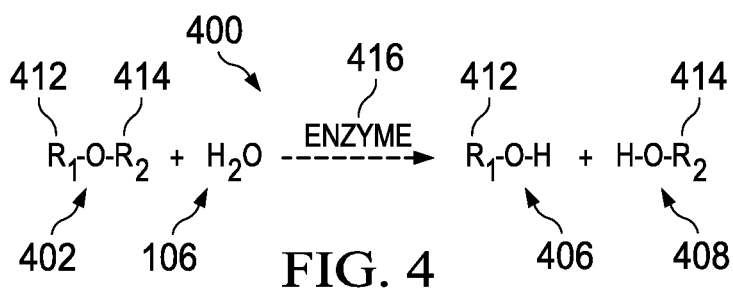
FIG. 4 is a chemical equation illustrating one embodiment of the invention comprising starch hydrolysis.

In some embodiments, the hydrolysis reaction is a starch-hydrolysis reaction 400 and the reagent comprises starch (e.g., starch molecule 402, as illustrated in FIG. 4). Further, in some embodiments, a composition (e.g., a slurry) comprises the starch and a liquid, and the starch is gelatinized, hydrated, and dispersed (e.g., suspended) in the liquid.

As an illustration of gelatinization, starch naturally has a fairly granular structure, but after gelatinization the structure becomes more open and expands. For example, when the granular starch is heated in the presence of water 106, the starch absorbs the water 106 (e.g., water 106 gets into the interstitial space of the starch). The water 106 opens up the starch and causes it to expand. In one embodiment, once the starch has been gelatinized, even if it is later dried, the starch retains a structure that is more open and more expanded than the original granular structure of the starch. Accordingly, in one embodiment, once starch has been gelatinized, it is easier to hydrate in the future. For example, in one embodiment, to hydrate a dry starch that has not yet been gelatinized and hydrated, the starch is mixed with (or dispersed in) water 106 and heated. However, in one embodiment, if a dry starch has been gelatinized and hydrated, it can be re-hydrated more easily (e.g., more quickly and without heat).

In one embodiment, even after a gelatinized starch is dried into powder 606, it retains a more open and expanded structure. For example, in one embodiment, gelatinized starch can be hydrated more easily (e.g., quicker and without as much or any heat) relative to ungelatinized starch.

In one embodiment, something is hydrated when it has absorbed liquid (e.g., a water-based liquid). In one embodiment, a starch and/or fiber is fully hydrated. For example, a composition comprising the starch and/or fiber has absorbed enough water 106 to reach its equilibrium water 106 activity at given conditions (e.g., temperature and pressure). In some embodiments, a starch and/or fiber is only partially hydrated. In some embodiments, starch and fiber or a composition comprising starch and fiber (e.g., grain flour) must be gelatinized in order to be hydrated. For example, in some embodiments, if the starch is not gelatinized, it can be dispersed into a liquid (e.g., water-based liquid) but it will settle (e.g., out or to the bottom of a container) of the liquid and will not remain dispersed in the liquid unless gelatinized. As another example, in some embodiments, if the starch and/or fiber is hydrated by a liquid, it has absorbed the liquid and can remain suspended in the liquid (e.g., indefinitely or for a longer period of time).

In some embodiments, a material is fully hydrated when it has absorbed enough liquid to achieve an equilibrium mass concentration of the liquid relative to the total weight of the material. In some embodiments, a composition comprising starch and/or fiber is essentially fully hydrated (e.g., having absorbed enough liquid to achieve, within about 3 weight percent, the equilibrium mass concentration of liquid). In some embodiments, the composition is substantially hydrated (e.g., having absorbed enough liquid to achieve, within about 50 weight percent, the equilibrium mass concentration of liquid). In some embodiments, the composition is noticeably hydrated (e.g., having absorbed enough liquid that increased hydration is detectable, for example, using appearance, increased mass, increased volume, expanded shape, decreased hardness, increased elasticity, a measurement, a sensor, etc.).

In some embodiments, the composition comprising the starch and/or fiber and a liquid has absorbed and/or been dispersed in enough liquid to be fluid-like (e.g., free-flowing under gravity and/or pumpable through a conduit 804, as depicted, for example, in FIG. 8). For example, in some embodiments, the composition has absorbed and/or been dispersed in enough liquid that the viscosity of the composition (while it can be relatively high compared to water 106 at 1 cP) is still sufficiently low to enable pumping the composition through a conduit 804.

In some embodiments, in order to hydrolyze a starch, the starch must be gelatinized and hydrated. In one embodiment, this is because, for example, an enzyme (e.g., α-amylase) used to catalyze the starch hydrolysis reaction 400 is more active when the starch is gelatinized.

Figure 2:
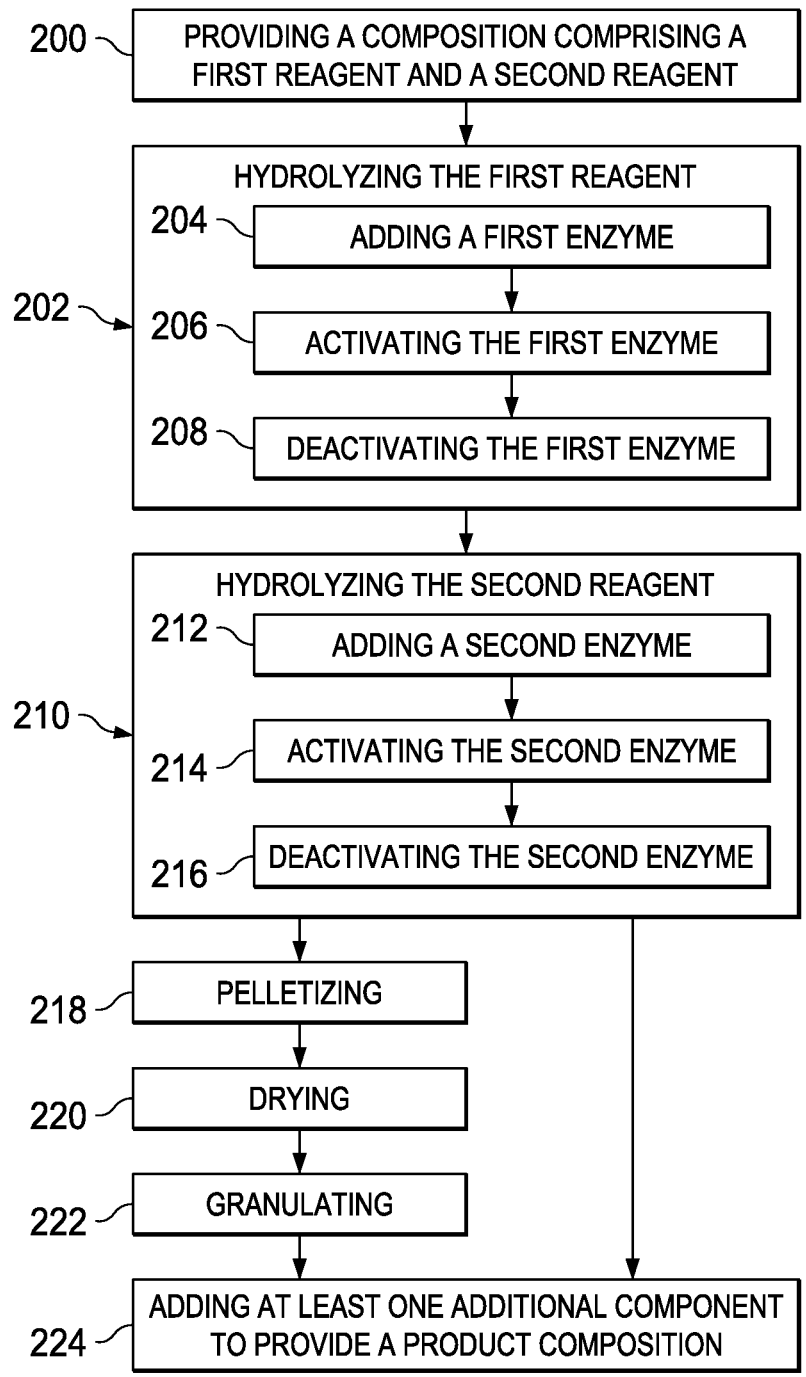
FIG. 2 is a schematic flow chart illustrating one embodiment of the invention comprising a first hydrolyzing step and a second hydrolyzing step.

One embodiment of the invention will now be described with reference to FIG. 2 which depicts a schematic flow chart illustrating a method for providing a product composition 122. As illustrated in FIG. 2, the method comprises a plurality of steps. First, a providing step 200 comprises providing a composition comprising a first reagent 108 and a second reagent 109. Second, a first hydrolyzing step 202 comprises hydrolyzing the first reagent 108 to provide a hydrolyzed composition 118 (e.g., the first hydrolyzed product 1210), as depicted, for example, in FIG. 12. Third, a second hydrolyzing step 210 comprises hydrolyzing the second reagent 109 to provide a hydrolyzed composition 118 (e.g., the second hydrolyzed product 1310, as depicted, for example, in FIG. 13). In some embodiments, the method comprises a plurality of hydrolyzing steps (e.g., the first hydrolyzing step 202 and the second hydrolyzing step 210) and the hydrolyzed composition 118 comprises a plurality of hydrolyzed products (e.g., the first hydrolyzed product 1210 and the second hydrolyzed product 1310). In some embodiments, the hydrolyzed composition 118 is a product composition 122.

In some embodiments, the hydrolyzed composition 118 is further processed and the method comprises additional steps, for example, as follow. Fourth, a pelletizing step 218 comprises pelletizing a hydrolyzed composition 118 comprising the first hydrolyzed product 1210 of the first hydrolyzing step 202 and/or the second hydrolyzed product 1310 of the second hydrolyzing step 210, thereby providing a pelletized mixture 602, as depicted, for example, in FIG. 6. Fifth, a drying step 220 comprises drying the pelletized mixture 602 to provide a dried mixture 604. Sixth, a granulating step 222 comprises granulating the dried mixture 604 to provide a powder 606. Seventh, an ingredient adding step 224 comprises adding at least one additional component 608 (e.g., an ingredient) to provide a product composition 122.

Figure 15:
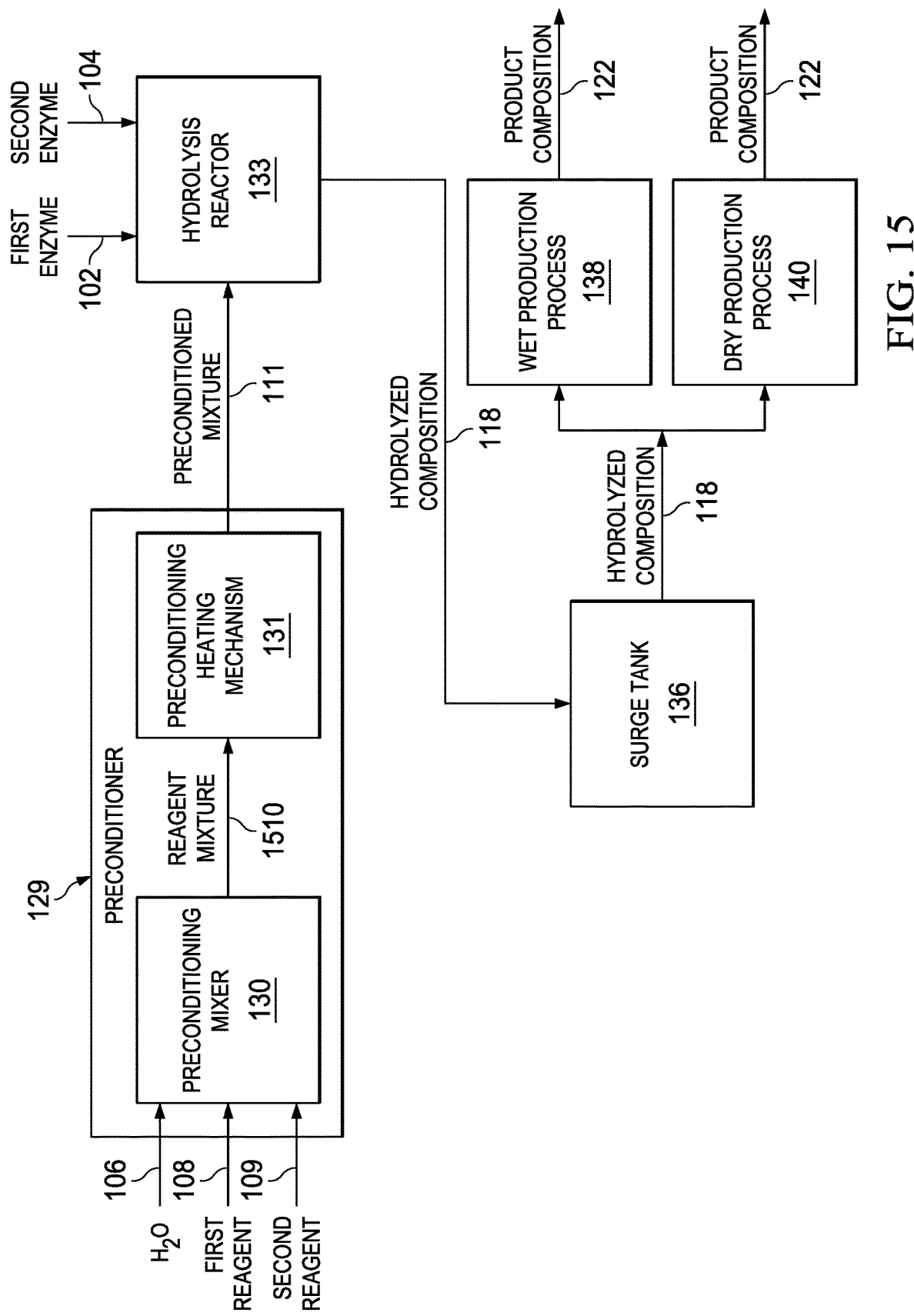
FIG. 15 is a block flow diagram illustrating one embodiment of the invention.

In some embodiments, the first hydrolyzing step 202 comprises a plurality of steps. For example, first, a first-enzyme adding step 204 comprises adding a first enzyme 102 to the composition comprising the first reagent 108, second reagent 109, third reagent, and/or some combination thereof to provide an enzyme-reagent mixture (e.g, a first enzyme-reagent mixture). Second, a first-enzyme activating step 206 comprises activating the first enzyme 102 (e.g., in the enzyme-reagent mixture) to provide a first hydrolysate intermediate composition 1208, as depicted, for example, in FIG. 12. Third, in a first deactivating step 208, the first enzyme 102 is deactivated to provide a composition comprising the first hydrolyzed product 1210. In some embodiments, the composition comprising the first hydrolyzed product 1210 is a product composition 122. Furthermore, in some embodiments, the composition comprising the first hydrolyzed product 1210 also comprises the second reagent 109 and is further processed using the second hydrolyzing step 210 or some portion thereof. Additionally, although the first-enzyme adding step 204 and the first-enzyme activating step 206 are illustrated sequentially, in some embodiments the steps occur simultaneously. For example, as illustrated in FIG. 15, if the composition comprising the first reagent 108, second reagent 109, third reagent, and/or some combination thereof (e.g., reagent mixture 1510) is heated before the first enzyme 102, second enzyme 104, third enzyme, and/or some combination thereof are/is added to the composition, the first enzyme, second enzyme, third enzyme, and/or some combination thereof can be activated when added to the composition. In some embodiments, the second hydrolyzing step 210 comprises a plurality of steps. First, a second-enzyme adding step 212 comprises adding a second enzyme 104 to the composition comprising the first reagent 108, second reagent 109, third reagent, and/or some combination thereof to provide an enzyme-reagent mixture (e.g, a second enzyme-reagent mixture). Second, a second-enzyme activating step 214 comprises activating the second enzyme 104 (e.g., in the enzyme-reagent mixture) to provide a second hydrolysate intermediate composition 1308, as depicted, for example, in FIG. 13. Third, in a second deactivating step 216, the second enzyme 104 is deactivated to provide a composition comprising the second hydrolyzed product 1310. In some embodiments, the composition comprising the second hydrolyzed product 1310 is a product composition 122. Furthermore, in some embodiments, the composition comprising the second hydrolyzed product 1310 also comprises the first reagent 108 and is further processed using the first hydrolyzing step 202 or some portion thereof. Additionally, although the second-enzyme adding step 212 and the second-enzyme activating step 214 are illustrated sequentially, in some embodiments the steps occur simultaneously. For example, if the composition comprising the first reagent 108, second reagent 109, third reagent, and/or some combination thereof is heated before the first enzyme 102, second enzyme 104, third enzyme, and/or some combination thereof are/is added to the composition, the first enzyme and/or second enzyme can be activated when added to the composition.

In some embodiments, the first-enzyme adding step or the second-enzyme adding step comprises adding endo-cellulase in an amount that provides about 30-200, about 100-130, or about 115 International Units (IU) of enzyme activity per gram of fiber. As used in this context, one IU is the amount of enzyme that will release 1 µmol per minute of reducing sugar from a composition comprising 1 wt. % carboxy-methyl cellulose (CMC) and a 99 wt. % solution of water and acid with a pH of 5, a temperature of 104° F. (40° C.) and a pressure of 1 atm. For example, citric acid can be added to provide the desired pH and to act as a buffer.

In some embodiments, the first-enzyme adding step or the second-enzyme adding step comprises adding α-amylase to provide about 600-3100, about 1700-2000, or about 1,850 Modified Wohlgemuth Units (MWU) of enzyme activity per gram of starch. As used in this context, one MWU is the amount of enzyme activity that will dextrinize 1 milligram (mg) of soluble starch to specified dextrins in 30 minutes under specified conditions. The specified dextrins and specified conditions are according to Valley Research Assay No. 511.003, available from Valley Research, Inc. of South Bend, Ind., US, which was acquired by Royal DSM N.V. of Herleen, the Netherlands.

Figure 12:
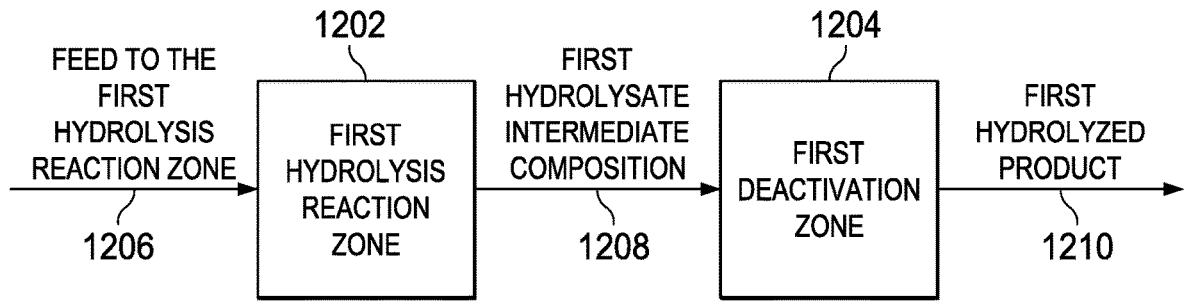
FIG. 12 is a block flow diagram illustrating one embodiment of the invention comprising a first hydrolysis reaction zone upstream of a first deactivation zone.
Figure 13:
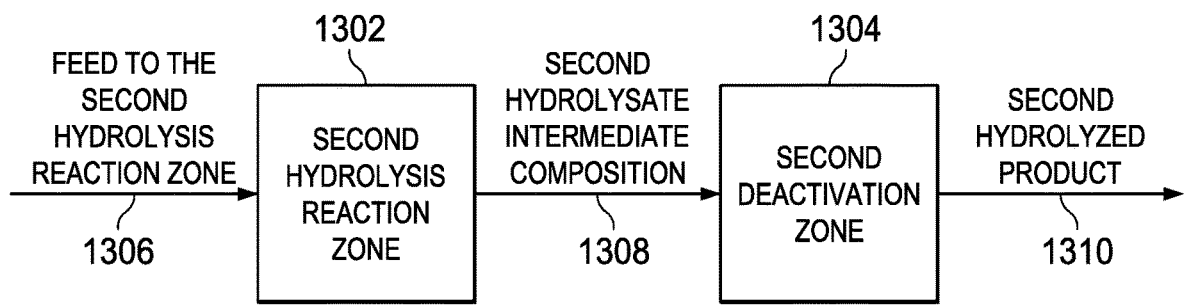
FIG. 13 is a block flow diagram illustrating one embodiment of the invention comprising a second hydrolysis reaction zone upstream of a second deactivation zone.

Although illustrated sequentially in FIG. 2, in some embodiments, the first hydrolyzing step 202 and the second hydrolyzing step 210 can overlap in time or occur simultaneously. Furthermore, in some embodiments, the first hydrolyzing step 202 and the second hydrolyzing step 210 occur in the same portions, overlapping portions, or different portions of a preconditioner 129 and/or a hydrolysis reactor 133. Additionally, in some embodiments, the first-enzyme adding step 204 and the second-enzyme adding step 212 occur simultaneously, the first-enzyme activating step 206 begins before the second-enzyme activating step 214, the first deactivating step 208 begins before the second deactivating step 216, and the first deactivating step 208 and the second deactivating step 216 overlap. Furthermore, in some embodiments, the first deactivating step 208 finishes before the second deactivating step 216 or finishes at the same time as the second deactivating step 216 (e.g., when deactivating steam is added to the first hydrolysate intermediate composition 1208 and/or the second hydrolysate intermediate composition 1308, which are illustrated in FIG. 12 and FIG. 13, respectively.

Figure 3:
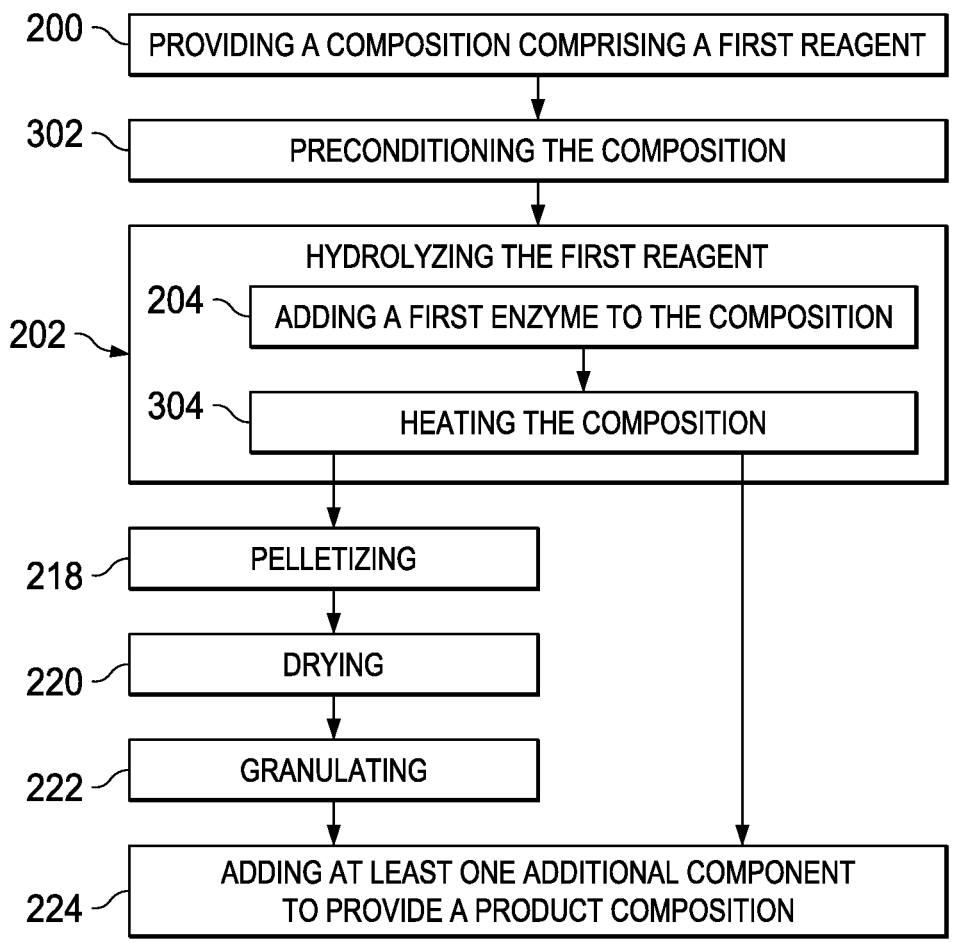
FIG. 3 is a schematic flow chart illustration one embodiment of the invention comprising a first hydrolyzing step.

One embodiment of the invention will now be described with reference to FIG. 3, which depicts a schematic flow chart illustrating a method for providing a product composition 122. The method is similar to the method illustrated in FIG. 2; however, the method of FIG. 3 illustrates a preconditioning step 302. Furthermore, although the method of FIG. 2 does not expressly illustrate a preconditioning step 302, FIG. 2 can also comprise a preconditioning step 302. Additionally, although the method illustrated in FIG. 3 does not expressly depict a second reagent 109, second enzyme 104, or second hydrolyzing step 210, the method can comprise these elements as appropriate.

As illustrated, the method of FIG. 3 comprises a plurality of steps. First, a providing step 200 comprises providing a composition comprising a first reagent 108. Second, a preconditioning step 302 comprises preconditioning the composition to provide a preconditioned mixture 111. Third, a first hydrolyzing step 202 comprises hydrolyzing the first reagent 108 in the preconditioned mixture 111 to provide a hydrolyzed composition 118. Fourth, a pelletizing step 218 comprises pelletizing the hydrolyzed composition 118 to provide a pelletized mixture 602. Fifth, a drying step 220 comprises drying the pelletized mixture 602 to provide a dried mixture 604. Sixth, a granulating step 222 comprises granulating the dried mixture 604 to provide a powder 606. Seventh, an ingredient adding step 224 comprises adding at least one additional component 608 to the powder 606 to provide a product composition 122.

In some embodiments, the first hydrolyzing step 202 comprises a plurality of steps as follows. First, a first-enzyme adding step 204 comprises adding a first enzyme 102 to the composition to provide an enzyme-reagent mixture 110 (e.g., a first enzyme mixture). Second, a composition heating step 304 comprises heating the composition (e.g., the enzyme-reagent mixture 110). In some embodiments, as the heating progresses, the composition is heated to a desired wet-mix temperature to provide a preconditioned mixture 111. Then, in some embodiments, as the heating continues, the composition (e.g., the preconditioned mixture 111) is hydrolyzed in a first hydrolysis reaction to provide a first hydrolysate intermediate composition 1208. The composition is intermediate, for example, because the first hydrolysis reaction in the composition has not yet reached a target percent conversion. Then, in some embodiments, as the heating continues, the composition (e.g., the first hydrolysate intermediate composition 1208) is deactivated to provide a hydrolyzed composition 118 (e.g., with the target percent conversion, which can be a range).

As illustrated in FIG. 3, the preconditioning step 302 occurs before the first-enzyme adding step 204 to provide the composition comprising the first reagent 108 with a desirable moisture content and temperature for the first enzyme 102 to catalyze the first hydrolysis reaction. Accordingly, in some embodiments, as soon as the first enzyme 102 is added to the composition comprising the first reagent 108, the first enzyme 102 is active. Thus, in some embodiments, the first-enzyme adding step 204 and the first-enzyme activating step 206 are simultaneous.

Although, in some embodiments, the composition comprising the first reagent 108 also comprises a first enzyme (e.g., a starch-hydrolysis-catalyzing enzyme 102), and the composition is heated to activate the first enzyme 102 as illustrated, for example, in FIG. 2. Additionally, although FIG. 3 only shows a first hydrolyzing step 202, some embodiments also include a second hydrolyzing step 210, for example, as illustrated in FIG. 2.

One embodiment of the invention will now be described with reference to FIG. 4, which illustrates a starch hydrolysis reaction 400 in which starch (e.g., a starch molecule 402) is converted to a hydrolyzed product, for example, hydrolyzed starch (e.g., a first hydrolyzed starch molecule 406 and a second hydrolyzed starch molecule 408). As illustrated, a starch molecule 402 comprises a first starch moiety 412 and a second starch moiety 414, and after an enzyme-catalyzed starch hydrolysis reaction 400, the first starch moiety 412 forms part of a first hydrolyzed starch molecule 406, and the second starch moiety 414 forms part of a second hydrolyzed starch molecule 408. Stoichiometrically, the reactants of the starch hydrolysis reaction 400 comprise a starch molecule 402 and water 106; the hydrolyzed products comprise a first hydrolyzed starch molecule 406 and a second hydrolyzed starch molecule 408; and the catalyst is a starch-hydrolysis-catalyzing enzyme molecule 416 (e.g., α-amylase). For example, in some embodiments, the starch molecule 402 is hydrolyzed into a first portion of hydrolyzed starch (e.g., a first hydrolyzed starch molecule 406) and a second portion of hydrolyzed starch (e.g., second hydrolyzed starch molecule 408).

One embodiment of the invention will now be described with reference to FIG. 5, which illustrates a fiber hydrolysis reaction 500 in which fiber (e.g., a fiber molecule 502) is converted to a hydrolyzed product, for example, hydrolyzed fiber (e.g., a first hydrolyzed fiber molecule 506 and a second hydrolyzed fiber molecule 508). As illustrated, a fiber molecule 502 comprises a first fiber moiety 512 and a second fiber moiety 514, and after an enzyme-catalyzed fiber hydrolysis reaction 500, the first fiber moiety 512 forms part of a first hydrolyzed fiber molecule 506 and the second fiber moiety 514 forms part of a second hydrolyzed fiber molecule 508. Stoichiometrically, the reactants of the fiber hydrolysis reaction 500 comprise a fiber molecule 502 and water 106; the products comprise a first hydrolyzed fiber molecule 506 and a second hydrolyzed fiber molecule 508; and the catalyst is a fiber-hydrolysis-catalyzing enzyme molecule 516 (e.g., endo-glucanase, or endo-cellulase). For example, in some embodiments, the fiber molecule 502 is hydrolyzed into a first portion of hydrolyzed fiber (e.g., a first hydrolyzed fiber molecule 506) and a second portion of hydrolyzed fiber (e.g., second hydrolyzed fiber molecule 508).

One embodiment of the invention will now be described with reference to FIG. 8, which depicts a schematic illustration of an apparatus comprising a hydrolysis reactor 133 for providing a product composition 122. As illustrated in FIG. 8, the hydrolysis reactor 133 comprises a conduit 804 for a composition comprising a first reagent 108. The conduit 804 comprises a composition inlet 808, a first enzyme inlet 806 downstream of the composition inlet 808 and a deactivating mechanism (e.g., a deactivating heater 132) downstream of the first enzyme inlet 806. As illustrated, the first enzyme inlet 806 provides a path of fluid communication between the conduit 804 and a source for a composition comprising the first enzyme 102. For example, this enables the first enzyme 102 to be added to the composition comprising the first reagent 108.

One embodiment of the invention will now be described with reference to FIG. 9, which depicts a schematic illustration of an apparatus comprising a hydrolysis reactor 133 for providing a product composition 122. The embodiment of FIG. 9 is generally similar to the embodiment of FIG. 8, although there are some differences. For example, in FIG. 9, the deactivating mechanism comprises a deactivating fluid inlet 904. Accordingly, in some embodiments a deactivating step comprises adding a deactivating fluid 902 to a composition comprising the first reagent 108 and the first enzyme 102, thereby deactivating the first enzyme 102. In some embodiments, the deactivating fluid 902 comprises a hot fluid, for example, steam, that heats the first enzyme 102 to deactivate it.

Figure 10:
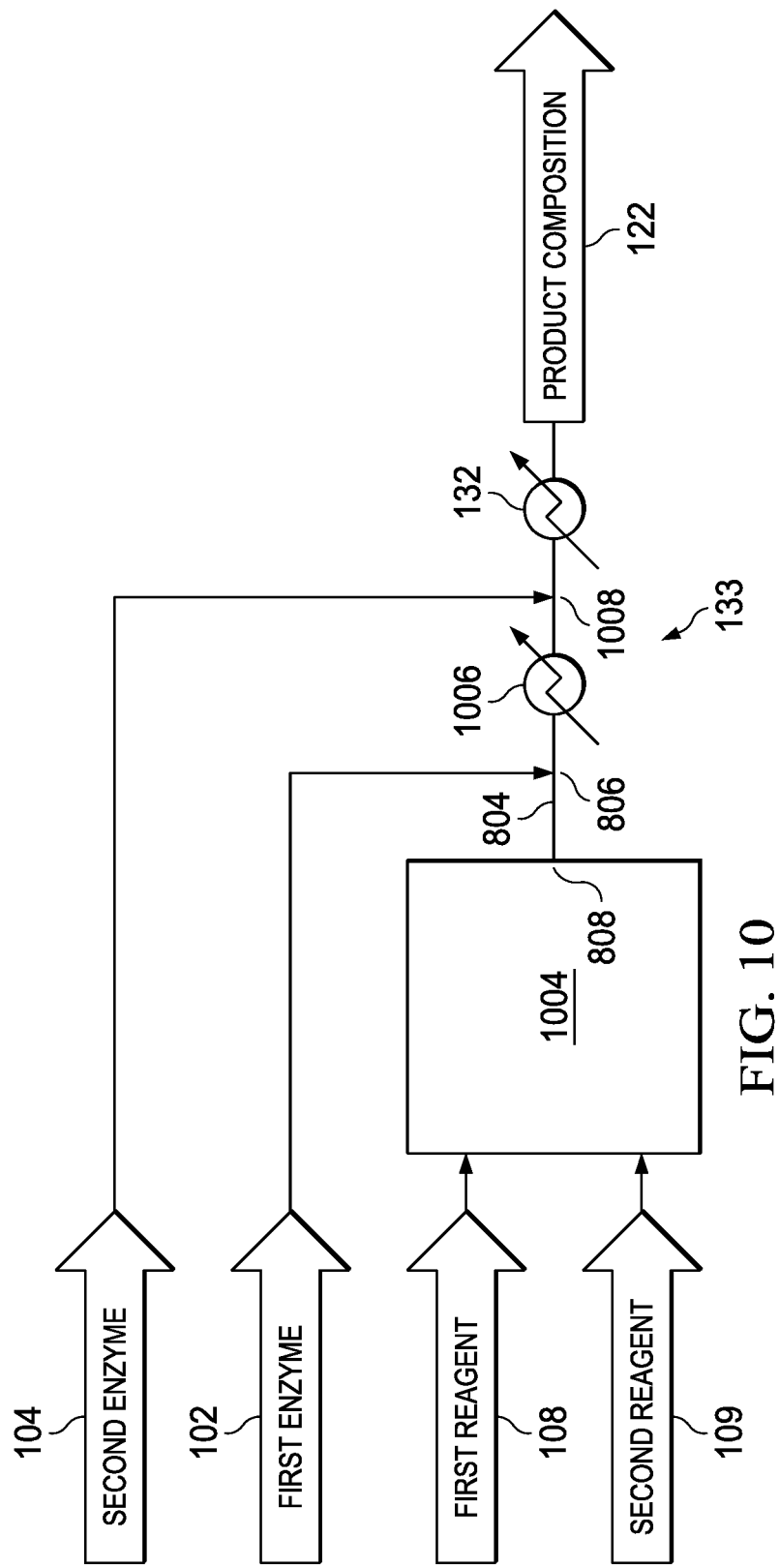
FIG. 10 is a schematic process flow diagram illustrating one embodiment of the invention comprising a plurality of enzymes, a source for a composition comprising a plurality of reagents, an intermediate heater between an inlet for a first enzyme and an inlet for a second enzyme, and a deactivating heater for deactivating at least one enzyme.

One embodiment of the invention will now be illustrated with reference to FIG. 10, which depicts a schematic illustration of an apparatus comprising a hydrolysis reactor 133 for providing a product composition 122. The embodiment of FIG. 10 is generally similar to the embodiment of FIG. 8, although there are some differences. For example, the embodiment of FIG. 9 further comprises a source 1004 (e.g., a tank or a pump) for the composition comprising the first reagent 108. Furthermore, the source is in fluid communication with the first reagent 108 and a second reagent 109. Accordingly, the source provides a composition that comprises the first reagent 108 and the second reagent 109 to the composition inlet 808 of the conduit 804.

With reference again to FIG. 10, the illustrated embodiment comprises an intermediate heater 1006 downstream of the first enzyme inlet 806. For example, the intermediate heater 1006 can be a jacket for gradually heating the composition as the composition flows through the pipe adjacent to the intermediate heater 1006. The intermediate heater 1006 can also be an infrared device, a microwave device, an ultrasonic device, or a heat exchanger.

Additionally, in the embodiment of FIG. 10, the conduit 804 comprises a second enzyme inlet 1008 downstream of the intermediate heater 1006. As illustrated, the second enzyme inlet 1008 is also upstream of the deactivating mechanism (e.g., the deactivating heater 132).

Moreover, some embodiments include a first deactivating mechanism (e.g., a deactivating heater 132, which is not explicitly shown in FIG. 10) downstream of the first enzyme inlet 806 and a second deactivating mechanism (e.g., deactivating heater 132) downstream of the second enzyme inlet 1008. Additionally, in some embodiments a third deactivating mechanism can be included downstream of a third enzyme inlet (not shown). Accordingly, although a plurality of enzymes can be deactivated by a deactivating mechanism, in some embodiments, the first enzyme 102 is deactivated by the first deactivating mechanism and the second enzyme 104 is deactivated by the second deactivating mechanism. Furthermore, in some embodiments, a third enzyme is deactivated by the third deactivating mechanism. Also, in some embodiments, the intermediate heater 1006 can be (or can be replaced by) a deactivating mechanism (e.g., deactivating heater 132 or a deactivating fluid inlet 904).

Figure 11:
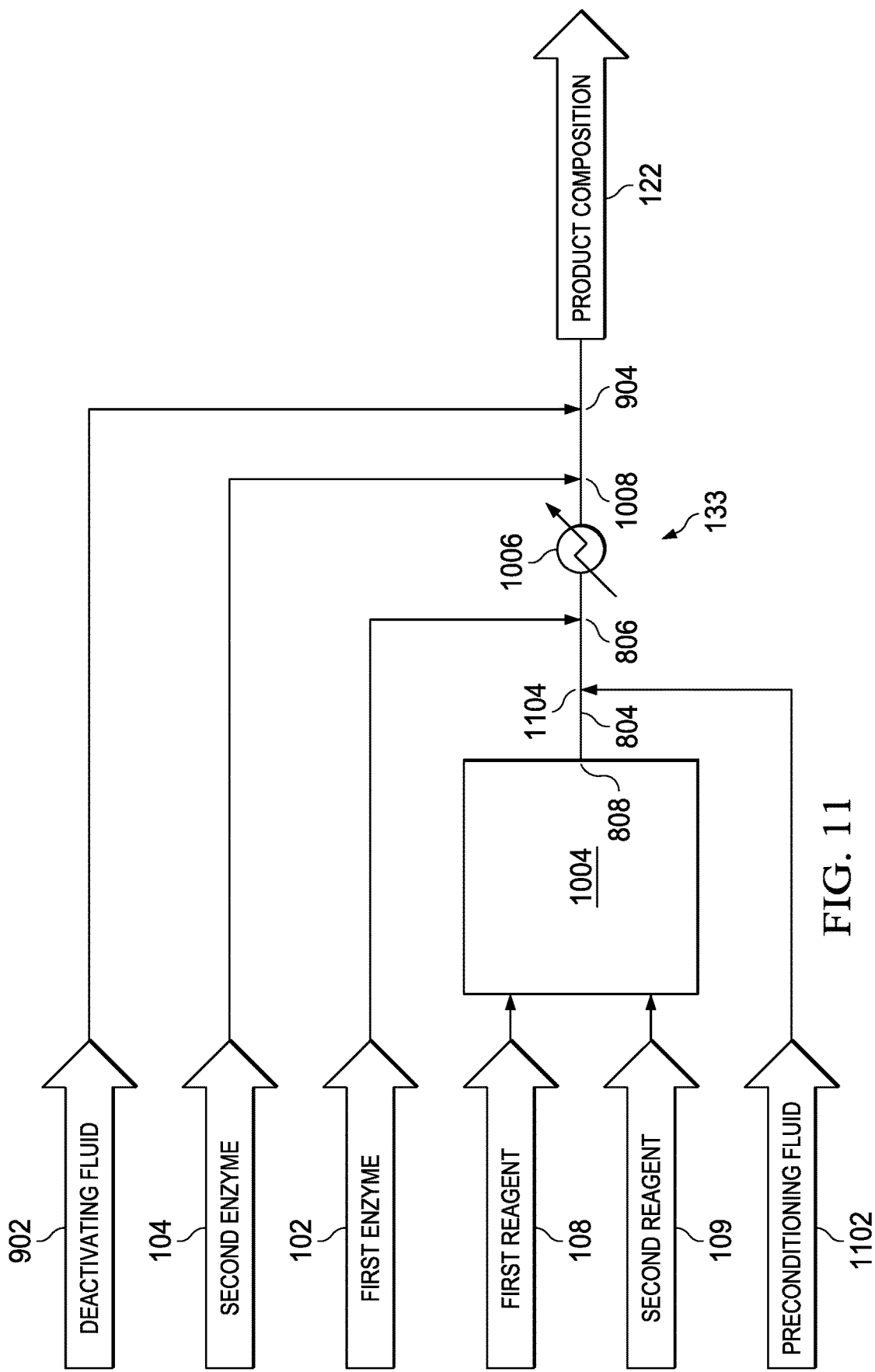
FIG. 11 is a schematic process flow diagram illustrating one embodiment of the invention comprising a plurality of enzymes, a source for a composition comprising a plurality of reagents, an inlet for a preconditioning fluid upstream of an inlet for a first enzyme, an intermediate heater between the inlet for the first enzyme and an inlet for a second enzyme, and an inlet for a deactivating fluid for deactivating at least one enzyme.

One embodiment of the invention will now be illustrated with reference to FIG. 11, which depicts a schematic illustration of an apparatus comprising a hydrolysis reactor 133 for providing a product composition 122. The embodiment of FIG. 11 is generally similar to the embodiment of FIG. 10, although there are some differences. For example, in the embodiment of FIG. 10, the deactivating mechanism comprises a deactivating fluid inlet 904 for a deactivating fluid 902 rather than a deactivating heater 132. Additionally, in the embodiment of FIG. 11, the conduit 804 comprises a preconditioning fluid inlet 1104 downstream of the composition inlet 808 and upstream of the first enzyme inlet 806.

One embodiment of the invention will now be described with reference to FIG. 12, which is a schematic illustration of a first hydrolysis reaction zone 1202 and a first deactivation zone 1204. In some embodiments, the first hydrolysis reaction zone 1202 begins where the first enzyme 102 is activated to hydrolyze the first reagent 108 and ends where the first deactivation zone 1204 begins. In some embodiments, the first deactivation zone 1204 begins at the location of a deactivating mechanism (e.g., a deactivating fluid inlet 904 or a deactivating heater 132). In some embodiments, the first deactivation zone 1204 ends where the deactivation of the first enzyme 102 is substantially complete, essentially complete, or complete. For example, when a composition comprising the first enzyme 102 reaches a deactivation temperature, the enzyme can be denatured (e.g., substantially or completely), and thereby deactivated. Accordingly, in some embodiments, the deactivation zone ends when the composition comprising the first enzyme 102 reaches the deactivation temperature.

Moreover, some embodiments include a first deactivating mechanism (e.g., a deactivating fluid inlet 904, which is not explicitly shown in FIG. 10) downstream of the first enzyme inlet 806 and a second deactivating mechanism (e.g., deactivating fluid inlet 904) downstream of the second enzyme inlet 1008. Accordingly, although a plurality of enzymes can be deactivated by a deactivating mechanism, in some embodiments, the first enzyme 102 is deactivated by the first deactivating mechanism and the second enzyme 104 is deactivated by the second deactivating mechanism. Also, in some embodiments, the intermediate heater 1006 can be (or can be replaced by) a deactivating mechanism (e.g., a deactivating heater 132 or a deactivating fluid inlet 904).

As illustrated in FIG. 12, first, feed 1206 to the first hydrolysis reaction zone 1202 is fed to the first hydrolysis reaction zone 1202 to provide a first hydrolysate intermediate composition 1208. Second, the first hydrolysate intermediate composition 1208 is fed to the first deactivation zone 1204 to provide a first hydrolyzed product 1210.

In some embodiments, the feed 1206 to the first hydrolysis reaction zone 1202 comprises a first reagent 108, and in the first hydrolysis reaction zone 1202, the hydrolysis of the first reagent 108 is catalyzed by a first enzyme 102 to provide the first hydrolysate intermediate composition 1208. Then, as the first hydrolysate intermediate composition 1208 is fed to the first deactivation zone 1204, the enzyme is deactivated and, accordingly, the first hydrolysis reaction stops (e.g., substantially or completely), thereby providing the first hydrolyzed product 1210 with a target percent conversion.

In some embodiments, the hydrolysis reactor 133 comprises the first hydrolysis reaction zone 1202 and the first deactivation zone 1204. Accordingly, in some embodiments the feed 1206 to the first hydrolysis reaction zone 1202 is a preconditioned mixture 111.

In some embodiments, a preconditioner 129 and a hydrolysis reactor 133 comprise the first hydrolysis reaction zone 1202 and the first deactivation zone 1204. For example, in some embodiments, the first hydrolysis reaction zone 1202 begins in a preconditioner 129 and ends in a hydrolysis reactor 133. Accordingly, in some embodiments the feed 1206 to the first hydrolysis reaction zone 1202 is a composition comprising the first reagent 108 and the first enzyme 102. Additionally, in some embodiments the enzyme can become more activated throughout the preconditioner 129 as the preconditioner 129 provides the composition and/or enzyme a desired wet-mix temperature and moisture content, and thereby provides a desired hydrolysis reaction rate by the time a composition comprising the enzyme leaves the preconditioner 129.

One embodiment will now be described with reference to FIG. 13. As illustrated in FIG. 13, first, feed 1306 to the second hydrolysis reaction zone 1302 is fed to the second hydrolysis reaction zone 1302 to provide a second hydrolysate intermediate composition 1308. Second, the second hydrolysate intermediate composition 1308 is fed to the second deactivation zone 1304 to provide a second hydrolyzed product 1310.

In some embodiments, the feed 1306 to the second hydrolysis reaction zone 1302 comprises a second reagent 109, and in the second hydrolysis reaction zone 1302, the hydrolysis of the second reagent 109 is catalyzed by a second enzyme 104 to provide the second hydrolysate intermediate composition 1308. Then, as the second hydrolysate intermediate composition 1308 is fed to the second deactivation zone 1304, the enzyme is deactivated and, accordingly, the second hydrolysis reaction substantially stops (e.g., substantially or completely), thereby providing the second hydrolyzed product 1310 with a target percent conversion.

In some embodiments, the hydrolysis reactor 133 comprises the second hydrolysis reaction zone 1302 and the second deactivation zone 1304. Accordingly, in some embodiments the feed 1306 to the second hydrolysis reaction zone 1302 is a preconditioned mixture 111.

In some embodiments, a preconditioner 129 and a hydrolysis reactor 133 comprise the second hydrolysis reaction zone 1302 and the second deactivation zone 1304. For example, in some embodiments, the second hydrolysis reaction zone 1302 begins in a preconditioner 129 and ends in a hydrolysis reactor 133. Accordingly, in some embodiments the feed 1306 to the second hydrolysis reaction zone 1302 is a composition comprising the second reagent 109 and the second enzyme 104. Additionally, in some embodiments the enzyme can become more activated throughout the preconditioner 129 as the preconditioner 129 provides the composition and/or enzyme with a desired wet-mix temperature and moisture content, and thereby provides a desired hydrolysis reaction rate by the time a composition comprising the enzyme leaves the preconditioner 129.

In some embodiments, the first deactivation zone 1204 is downstream of the first hydrolysis reaction zone 1202. In some embodiments, the second deactivation zone 1304 is downstream of the second hydrolysis reaction zone 1302. Furthermore, in some embodiments, the first hydrolysis reaction zone 1202 can be positioned upstream of, be positioned to overlap fully or in part, or be positioned downstream of the second hydrolysis reaction zone 1302 and/or the second deactivation zone 1304. Additionally, in some embodiments, the second hydrolysis reaction zone 1302 can be positioned upstream of, be positioned to overlap fully or in part, or be positioned downstream of the first hydrolysis reaction zone 1202 and/or the first deactivation zone 1204. In some embodiments, the positions of the various zones can be rearranged as appropriate depending on the conditions (e.g., moisture content, and temperature) in the preconditioner 129, and/or the hydrolysis reactor 133.

In some embodiments, the conduit 804, the preconditioner 129, and/or the hydrolysis reactor 133 are compact, lightweight, and/or mobile. In some embodiments, a module comprises the conduit 804, the preconditioner 129, the hydrolysis reactor 133, and/or some combination thereof. For example, in some embodiments, the module takes up no more than a cubic volume defined by common sizes of semi-trailers. For example, in some embodiments, the module has a product flow rate of 10,000 kg/h (+/−20%) and takes up no more space than (or fits inside) a cubic volume defined by a width selected from no more than about 2.44 m (8 ft) or 2.6 m (8 ft 6.4 inches), a length selected from no more than about 8.53 m (28 ft), 9.75 m (32 ft), 10.36 m (34 ft), 10.97 m (36 ft), 12.19 m (40 ft), 13.72 m (45 ft), 14.63 m (48 ft), 16.15 m (53 ft), and 17.37 m (57 ft) m, and a height selected from no more than about 4.11 m (13.5 ft) or 4.27 m (14 ft). In some embodiments, the module takes up no more space than a cubic volume selected from about 85.63 cubic meters ("cu. m.") (3024 cubic feet ("cu. ft.")), 88.80 cu. m. (3136 cu. ft.), 91.339 cu. m. (3225.6 cu. ft), 94.722 cu. m. (3345.1 cu. ft.), 174.32 cu. m. (6156 cu. ft.), 180.77 cu. m. (6384 cu. ft.), 185.940 cu. m. (6566.4 cu. ft.), or 192.826 cu. m. (6809.6 cu. ft.). As another example, in some embodiments the product flow rate divided by the volume of the module is at least about 116 kg/m$^3$/h+/−20% (e.g., about 10,000 kg/h divided by 85.63 m$^3$). Additionally, in some embodiments, the module can be permanently or removably fixed on a skid for transporting the hydrolysis reactor 133 from one manufacturing facility to another. Although embodiments have been described with reference to listed values (e.g., individual values and ranges), it should be understood that for any values listed herein, additional embodiments can be formed from any values or ranges contained within the listed values and/or between listed values. For example, if a parameter is described as having a value of no more than about 2.44 m or 2.6 m then, in some embodiments, the parameter can also vary, for example, from 1-2.5 m or from 2.5-2.6 m, as a skilled person would understand after reading the present disclosure.

One embodiment of the invention will now be described with reference to FIG. 15, which illustrates a block flow diagram for hydrolyzing a first reagent 108 (e.g., fiber) and a second reagent 109 (e.g., starch) to provide a product composition 122.

As illustrated in FIG. 15, reaction components selected from the group consisting of water 106, a first reagent 108, a second reagent 109, and some combination thereof are mixed in a preconditioning mixer 130 to provide a reagent mixture 1510. The reagent mixture 1510 is fed to a preconditioning heating mechanism 131 (e.g., preconditioning fluid inlet 1104 or preconditioning heater) to provide a preconditioned mixture 111. In some embodiments, the preconditioning heater comprises an infrared device, a microwave device, an ultrasonic device, or a heat exchanger (e.g., a heat jacket). Additionally, in some embodiments, the preconditioning mixer 130 and the preconditioning heating mechanism 131 are combined, for example, in a preconditioner 129. Accordingly, in some embodiments mixing the reaction components to provide a reagent mixture 1510 and heating the reagent mixture 1510 to provide a preconditioned mixture 111 take place simultaneously in a preconditioning step 302.

With reference again to FIG. 15, the preconditioned mixture 111 is fed to a hydrolysis reactor 133 to provide a hydrolyzed composition 118. As illustrated, the first enzyme 102 and the second enzyme 104 are also fed to the hydrolysis reactor 133 or a plurality of hydrolysis reactors. Moreover, in some embodiments, the first hydrolysis reaction and second hydrolysis reaction begin at the point or points the first enzyme and second enzyme are added to the hydrolysis reactor 133 or a plurality of hydrolysis reactors. In some embodiments, the hydrolyzed composition 118 is fed to a surge tank 136, for example, to provide storage for the hydrolyzed composition 118 or to provide more control over the rate at which the hydrolyzed composition 118 is fed to any downstream processes. Furthermore, in some embodiments, the hydrolyzed composition 118 is fed to a wet production process 138 and/or a dry production process 140 to provide a product composition 122.

Although the embodiment is illustrated using a first reagent 108 and a second reagent 109, in some embodiments only the first reagent 108 or only the second reagent 109 are hydrolyzed. For example, in some embodiments, when only the first reagent 108 is hydrolyzed in a first hydrolysis reaction, the first enzyme 102 is used to catalyze the first hydrolysis reaction and the second enzyme 104 is unnecessary and is not used. As another example, in some embodiments, when only the second reagent 109 is hydrolyzed in a second hydrolysis reaction, only the second enzyme 104 is used to catalyze the second hydrolysis reaction.

Additionally, although illustrated separately in the embodiment shown in FIG. 15, in some embodiments a mixer (e.g., in a preconditioner 129) comprises both the preconditioning mixer 130 and the preconditioning heating mechanism 131. Accordingly, in some embodiments, the heating and the mixing occur simultaneously. Furthermore, in some embodiments the order of the preconditioning mixer 130 and the preconditioning heating mechanism 131 are interchanged. Also, in some embodiments, the order of the preconditioning heating and preconditioning mixing are interchanged.

Figure 16:
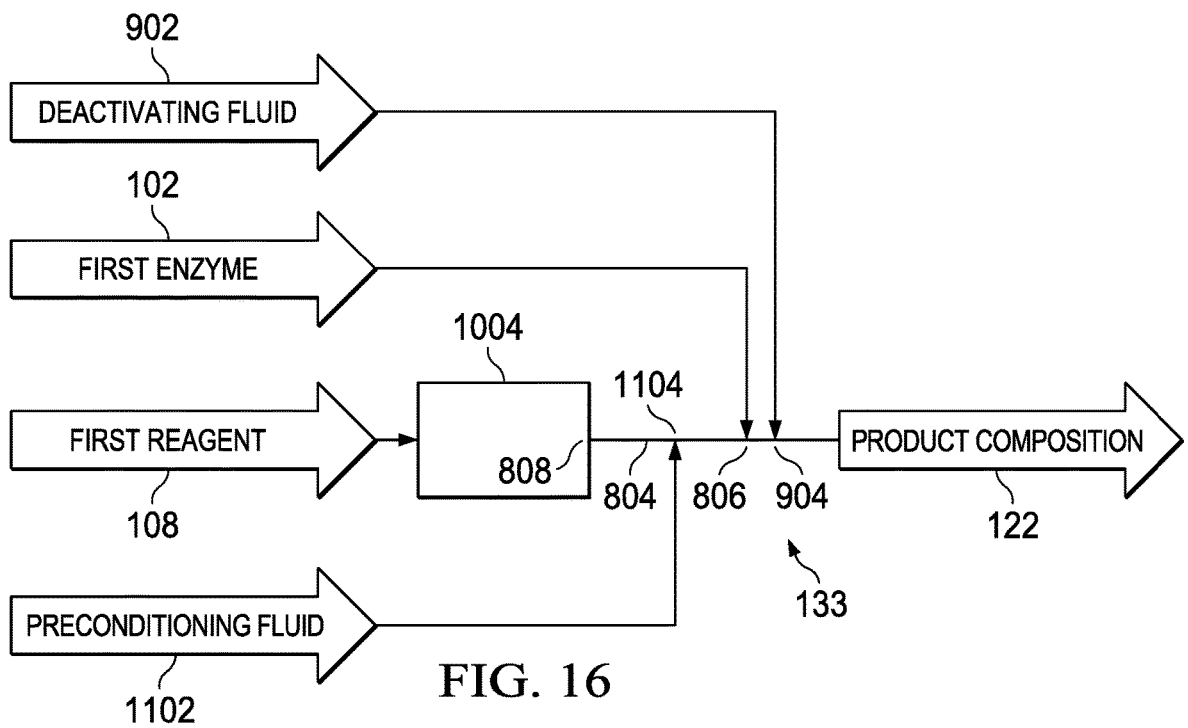
FIG. 16 is a schematic process flow diagram illustrating one embodiment of the invention comprising a source for a composition comprising a first reagent, an inlet for a preconditioning fluid upstream of an inlet for a first enzyme, and an inlet for a deactivating fluid for deactivating the first enzyme.

One embodiment of the invention will now be illustrated with reference to FIG. 16, which depicts a schematic illustration of an apparatus comprising a hydrolysis reactor 133 for providing a product composition 122. As illustrated in FIG. 16, the hydrolysis reactor 133 comprises a conduit 804 for a composition comprising a first reagent 108. The conduit 804 comprises a composition inlet 808, and a first enzyme inlet 806 downstream of the composition inlet 808 and a deactivating mechanism (e.g., a deactivating heater 132 or deactivating fluid inlet 90 as illustrated) downstream of the first enzyme inlet 806. The conduit 804 also comprises a preconditioning device (e.g., preconditioning fluid inlet 1104 or a preconditioning heater) upstream of the first enzyme inlet 806 and optionally downstream of a composition inlet 808 and/or a source 1004 (e.g., a tank or a pump) for the composition comprising the first reagent 108.

As illustrated, the first enzyme inlet 806 provides a path of fluid communication between the conduit 804 and a source for a composition comprising the first enzyme 102. For example, this enables the first enzyme 102 to be added to the composition comprising the first reagent 108.

Although, various selections of steps, elements, and features are described herein in a particular arrangement, in some embodiments, elements are added, elements are omitted, elements are interchanged between the embodiments, or elements are rearranged with respect to sequence, connectivity, or spatial placement as appropriate. A skilled person, upon reading this disclosure, would understand that all such modifications are encompassed by this disclosure.

As an example, while some embodiments only expressly illustrate elements for hydrolyzing a first reagent 108, the embodiment can be modified to hydrolyze a plurality of reagents (e.g., a first reagent 108, a second reagent 109, and/or a third reagent). Similarly, while some embodiments illustrate elements for hydrolyzing a first reagent 108 and a second reagent 109, the elements for hydrolyzing the second agent can be omitted, leaving only elements for hydrolyzing the first reagent 108.

As another example, while some embodiments do not expressly illustrate a source 1004 for the composition, the embodiments can comprise a source. Likewise, embodiments that do not expressly illustrate an intermediate heater 1006 can comprise an intermediate heater 1006, and the intermediate heater 1006 can be omitted from embodiments that expressly illustrate the intermediate heater 1006. Additionally, for embodiments using a deactivating mechanism, one type of deactivating mechanism can be interchanged for another type of deactivating mechanism.

COMPARATIVE EXAMPLES

Figure 14:
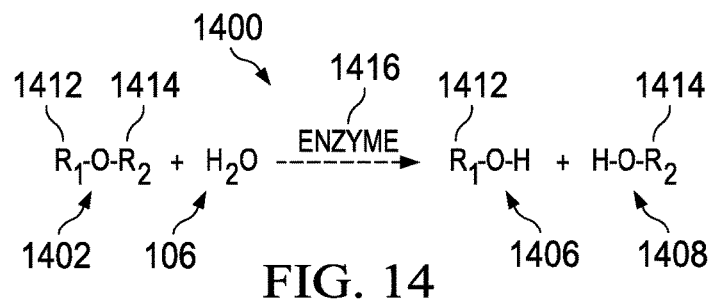
FIG. 14 is a chemical equation illustrating one embodiment of the invention comprising protein hydrolysis.

One embodiment of the invention will now be described with reference to FIG. 2, which illustrates a method for providing a product composition 122, for example, a food grade product composition 122. The method comprises hydrolyzing a first reagent 108 (e.g., fiber molecules 502 or starch molecules 402 or protein molecules 1402 as illustrated in FIG. 4, FIG. 5, and FIG. 14) in a first hydrolysis reaction (e.g., a fiber-hydrolysis reaction 500 or a starch-hydrolysis reaction 400 or a protein-hydrolysis reaction 1400). In addition, the method comprises deactivating a first enzyme 102 (e.g., a fibrolytic enzyme, endo-glucanase, endo-cellulase, α-amylase, or a protein-hydrolysis-catalyzing enzyme) catalyzing the first hydrolysis reaction. In some embodiments, as illustrated in FIG. 12, this produces a first hydrolyzed product 1210 with a first target percent conversion of the first reagent 108 to the first hydrolyzed product 1210. In some embodiments, the first hydrolyzed product 1210 is a composition comprising, consisting of, or consisting essentially of the products of the first hydrolysis reaction (e.g., the first hydrolyzed starch molecule 406 and the second hydrolyzed starch molecule 408 illustrated in FIG. 4, or the first hydrolyzed fiber molecule 506 and the second hydrolyzed fiber molecule 508 illustrated in FIG. 5, or the first hydrolyzed protein molecule 1406 and the second hydrolyzed protein molecule 1408 illustrated in FIG. 14).

With reference again to FIG. 2, some embodiments comprise hydrolyzing the first reagent 108 and hydrolyzing a second reagent 109 (e.g., fiber molecules 502 or starch molecules 402 or protein molecules 1402) in a second hydrolysis reaction (e.g., a fiber-hydrolysis reaction 500 or a starch-hydrolysis reaction 400 or a protein-hydrolysis reaction 1400). In addition, the method comprises deactivating a second enzyme 104 (e.g., fibrolytic enzymes, endo-glucanase, endo-cellulase, α-amylase, or protein-hydrolysis-catalyzing enzyme) catalyzing the second hydrolysis reaction. In some embodiments, this produces a second hydrolyzed product 1310 with a second target percent conversion of the second reagent 109 to the second hydrolyzed product 1310.

Figure 5:
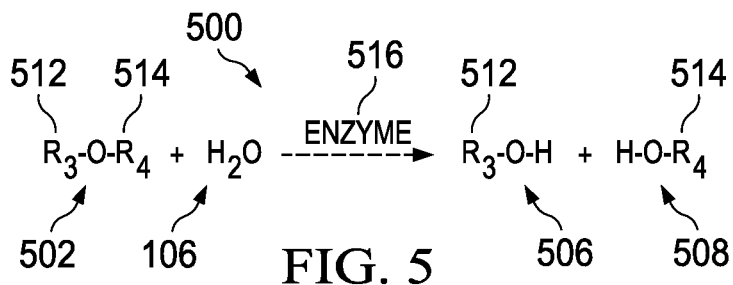
FIG. 5 is a chemical equation illustrating one embodiment of the invention comprising fiber hydrolysis.

In some embodiments, as illustrated in FIG. 13, the second hydrolyzed product 1310 is a composition comprising, consisting of, or consisting essentially of the products of the second hydrolysis reaction (e.g., the first hydrolyzed starch molecule 406 and the second hydrolyzed starch molecule 408 illustrated in FIG. 4, or the first hydrolyzed fiber molecule 506 and the second hydrolyzed fiber molecule 508 illustrated in FIG. 5, or the first hydrolyzed protein molecule 1406 and the second hydrolyzed protein molecule 1408 illustrated in FIG. 1400).

Accordingly, in some embodiments the first enzyme 102 comprises a fiber-hydrolysis-catalyzing enzyme 516 (e.g., fibrolytic enzymes, endo-glucanase, or endo-cellulase) or a starch-hydrolysis-catalyzing enzyme 416 (e.g., α-amylase), or a protein-hydrolysis-catalyzing enzyme. Similarly, in some embodiments the second enzyme 104 comprises a fiber-hydrolysis-catalyzing enzyme 516 (e.g., fibrolytic enzymes, endo-glucanase, or endo-cellulase), or a starch-hydrolysis-catalyzing enzyme 416 (e.g., α-amylase), or a protein-hydrolysis-catalyzing enzyme.

As another example, in some embodiments, the first reagent 108 is fiber (i.e., fiber molecules 502), the first hydrolysis reaction is a fiber-hydrolysis reaction 500, the first enzyme 102 is a fiber-hydrolysis-catalyzing enzyme 516, and the first hydrolyzed product 1210 comprises the products of the fiber-hydrolysis reaction 500 (e.g., the first hydrolyzed fiber molecule 506 and the second hydrolyzed fiber molecule 508 illustrated in FIG. 5). Meanwhile, the second reagent 109 is starch (i.e., starch molecules 402), the second hydrolysis reaction is a starch-hydrolysis reaction 400, the second enzyme 104 is starch-hydrolysis catalyzing enzyme 416, and the second hydrolyzed product 1310 comprises the products of the starch-hydrolysis reaction 400 (e.g., the first hydrolyzed starch molecule 406 and the second hydrolyzed starch molecule 408 illustrated in FIG. 5).

As another example, in some embodiments, the first reagent 108 or the second reagent 109 is protein. Additionally, in some embodiments a third reagent is protein (e.g., a protein molecule 1402 or plurality of protein molecules as illustrated in FIG. 14). Furthermore, in some embodiments the first enzyme 102 or the second enzyme 104 is a protein-hydrolysis-catalyzing enzyme. Moreover, in some embodiments a third enzyme is a protein-hydrolysis-catalyzing enzyme. In some embodiments, the protein-hydrolysis-catalyzing enzyme is an endo-enzyme. In some embodiments, deactivation temperature for protein-hydrolysis-catalyzing enzymes are the same as the deactivation temperatures for another enzyme, are higher than the deactivation temperature for the first enzyme, are lower than the deactivation temperature for the second enzyme, are higher than the second enzyme, are lower than the deactivation temperature for the third enzyme, or some combination thereof. In some embodiments, deactivation temperatures for protein-hydrolysis-catalyzing enzymes include, for example, about 70-100° C.

Additionally, the embodiments discussed herein can be modified to form additional embodiments in which protein is hydrolyzed in place of or in addition to another reagent (e.g., starch and/or fiber). As can be seen in FIG. 14, protein hydrolysis proceeds analogously to starch or fiber hydrolysis, which were illustrated in FIG. 4 and FIG. 5. FIG. 14 illustrates a protein hydrolysis reaction 1400 in which protein (e.g., a protein molecule 1402) is converted to a hydrolyzed product, for example, hydrolyzed protein (e.g., a first hydrolyzed protein molecule 1406 and a second hydrolyzed protein molecule 1408). As illustrated, a protein molecule 1402 comprises a first protein moiety 1412 and a second protein moiety 1414, and after an enzyme-catalyzed protein hydrolysis reaction 1400, the first protein moiety 1412 forms part of a first hydrolyzed protein molecule 1406, and the second protein moiety 1414 forms part of a second hydrolyzed protein molecule 1408. Stoichiometrically, the reactants of the protein hydrolysis reaction 1400 comprise a protein molecule 1402 and water 106; the hydrolyzed products comprise a first hydrolyzed protein molecule 1406 and a second hydrolyzed protein molecule 408; and the catalyst is a protein-hydrolysis-catalyzing enzyme molecule 1416 (e.g., alkalase, bromelain, and papain). For example, in some embodiments, the protein molecule 1402 is hydrolyzed into a first portion of hydrolyzed protein (e.g., a first hydrolyzed protein molecule 1406) and a second portion of hydrolyzed protein (e.g., second hydrolyzed protein molecule 1408).

With reference again to FIG. 2, a deactivating step (e.g., the first deactivating step 208 or the second deactivating step 216) can be accomplished using a variety of approaches. In some embodiments, the deactivating step is quick, for example, lasting no more than about 10 seconds, 5 seconds, 4 seconds, 3 seconds, 2 seconds, or 1 second. While the deactivating step can technically be designed to take longer, it can be useful to have the deactivating step occur nearly instantly throughout a desired portion of a composition. For example, as illustrated in FIG. 8, for a composition in the form of a composition stream in a conduit 804, it can be desirable to deactivate the enzyme distributed throughout a cross-section of the composition stream in no more than about 10 seconds, 5 seconds, 4 seconds, 3 seconds, 2 seconds, or 1 second. Although specific ranges are listed, as with the other ranges given herein, a skilled person with the benefit of this disclosure would also understand that additional ranges can be formed from values that are contained within the listed ranges and are considered to provide additional embodiments.

Additionally, with reference to FIG. 9, in some embodiments, the deactivating step comprises adding a deactivating fluid 902 to a composition comprising the first enzyme 102. Examples of a deactivating fluid 902 include a hot fluid, a liquid (e.g., water 106, milk, juice, oil, or melted butter), or a gas (e.g., steam). As an illustration, the deactivating fluid 902 can be used to deactivate an enzyme catalyzing a hydrolysis reaction. For example, the deactivating fluid 902 can be injected into a composition comprising the enzyme, thereby heating the fluid and deactivating the enzyme.

In some embodiments, the deactivating step comprises heating the first enzyme 102 using a deactivating mechanism. Examples of a deactivating mechanism include mixing a hot fluid (e.g., deactivating fluid 902) with the first enzyme 102 as illustrated in FIG. 9 or using a deactivating heater 132 to heat the first enzyme 102 as illustrated in FIG. 8. In some embodiments, the deactivating heater 132 can be any heating device, for example, an infrared device, a microwave device, an ultrasonic device, or a heat exchanger. Although, in some embodiments only a device that can heat the first enzyme 102 and/or second enzyme 104 quickly enough to deactivate the first enzyme 102 and/or second enzyme 104 within a desired deactivation time is used.

Various process conditions and variables can affect the rate and reaction time (e.g., duration) of a hydrolysis reaction. For example, the rate of a hydrolysis reaction in a composition can be faster when the composition has a higher mole concentration of enzyme, when the composition has a higher mole concentration of water 106, and when the composition has an optimum temperature or a temperature within an optimum temperature range.

Additionally, the overall reaction time of the hydrolysis reaction depends on the reaction rate, the desired extent of reaction (e.g., target degree of conversion), and how precisely in time the deactivation of the enzyme catalyzing hydrolysis can be achieved upon reaching the desired extent of reaction. In some embodiments, the reaction time of the hydrolysis reaction (e.g., from the time enzyme is added to start enzyme-catalyzed hydrolysis to the time the deactivating step is complete) is relatively shorter than the reaction time of the hydrolysis reaction in batch processes or extrusion processes. For example, this can enable faster production rates of a composition comprising a hydrolyzed component (e.g., starch and/or fiber). In some embodiments, the reaction time is no more than about 30 seconds, 10 seconds, or 5 seconds. As used herein, the reaction time is an average reaction time. For example, a reaction time of no more than about 30 seconds, 10 seconds, or 5 seconds means that, on average, a mass of a composition comprising the first reagent, the second reagent, and/or a third reagent spends no more than about 30 seconds, 10 seconds, or 5 seconds reacting as measured from activation or addition of an enzyme to the mass until deactivation of the enzyme in the mass.

With reference again to FIG. 2, in some embodiments, hydrolyzing the first reagent 108 and deactivating the first enzyme 102 occur in a conduit 804, for example, as depicted in FIGS. 8-11. Similarly, in some embodiments, hydrolyzing the second reagent 109 and deactivating the second enzyme 104 occur in the conduit 804.

In some embodiments, the first hydrolysis reaction and/or the second hydrolysis reaction occurs in a wet hydrolysis process. For example, in some embodiments, the first hydrolysis reaction and/or the second hydrolysis reaction occurs in a composition comprising at least 50 wt. %, 60 wt. %, 70 wt. %, 80 wt. %, 90 wt. %, or 95 wt. % liquid (e.g., water 106). As another example, in some embodiments, the composition comprises from about 50 wt. % to about 99 wt. % liquid, from about 70 wt. % to about 90 wt. % liquid, or from about 75 wt. % to about 85 wt. % liquid.

In some embodiments of the invention, a method provides a continuous process for providing a product composition 122. For example, the first hydrolysis reaction and/or second hydrolysis reaction can be part of a continuous hydrolysis process rather than a batch process. Additionally, in some embodiments, the first enzyme 102 and a composition comprising the first reagent 108 (e.g., an enzyme-reagent mixture 110 or preconditioned mixture 111) can be continuously fed to a first hydrolysis reaction zone 1202 (e.g., a first-enzyme-catalyzed-hydrolysis reaction zone). Furthermore, in some embodiments, the first enzyme 102 is continuously deactivated in a first deactivation zone 1204.

As illustrated, for example, in FIGS. 12 and 13, in some embodiments, the first deactivation zone 1204 begins downstream of where the first hydrolysis reaction zone 1202 begins. Similarly, in some embodiments, the second deactivation zone 1304 begins downstream of where the second hydrolysis reaction zone 1302 begins.

With reference again to FIG. 2, in some embodiments the first reagent 108 is fiber and deactivating the first enzyme 102 occurs before more than about 10, 9, 8, 7, 6, 5, 4, 3, 2, or 1 wt % of the first reagent 108 has been converted to non-fiber molecules (e.g., molecules selected from the group consisting of monosaccharides, disaccharides, and both monosaccharides and disaccharides).

Furthermore, in some embodiments the second reagent 109 is starch and deactivating the second enzyme 104 occurs before more than about 10, 9, 8, 7, 6, 5, 4, 3, 2, or 1 wt % of the second reagent 109 has been converted to non-starch molecules (e.g., molecules selected from the group consisting of monosaccharides, disaccharides, and both monosaccharides and disaccharides).

In some embodiments, little or no starch or fiber is converted to monosaccharides or disaccharides during hydrolysis. For example, in some embodiments, no starch in a composition is converted to monosaccharides or disaccharides during hydrolysis within a +/−10, 5, 4, 3, 2, or 1 wt. % tolerance (on a dry weight basis) of the measured weight percentage values of starch, monosaccharides and disaccharides in the composition. For example, after deactivating an enzyme catalyzing hydrolysis of the starch in a composition, the weight percentage of the starch in the composition after hydrolysis is equal to the weight percentage of the starch in the composition before hydrolysis within a +/−10, 5, 4, 3, 2, or 1 wt. % tolerance. For example, the tolerance can be measured relative to the weight percentage of the starch in the composition before hydrolysis on a dry weight basis.

In some embodiments, no fiber in a composition is converted to monosaccharides or disaccharides during hydrolysis within a +/−10, 5, 4, 3, 2, or 1 wt. % tolerance of the measured weight percentage values of fiber, monosaccharides and disaccharides in a composition after deactivating an enzyme catalyzing hydrolysis of the fiber in the composition. For example, after deactivating an enzyme catalyzing hydrolysis of the fiber in a composition, the weight percentage of the fiber in the composition after hydrolysis is equal to the weight percentage of the fiber in the composition before hydrolysis within a +/−10, 5, 3, or 1 wt. % tolerance. The tolerance can be measured relative to the weight percentage of the fiber in the composition before hydrolysis on a dry weight basis.

In some embodiments, no protein in a composition is converted to one or more amino acids during hydrolysis within a +/−10, 5, 4, 3, 2, or 1 wt. % tolerance of the measured weight percentage values of protein and/or amino acids in a composition after deactivating an enzyme catalyzing hydrolysis of the protein in the composition. For example, after deactivating an enzyme catalyzing hydrolysis of the protein in a composition, the weight percentage of the protein in the composition after hydrolysis is equal to the weight percentage of the protein in the composition before hydrolysis within a +/−10, 5, 3, or 1 wt. % tolerance. The tolerance can be measured relative to the weight percentage of the protein in the composition before hydrolysis on a dry weight basis.

In some embodiments, the weight percentage values are calculated on a dry basis (i.e., excluding any water 106 content). In some embodiments, the weight percentage values are calculated on a basis excluding any components that were not present in the composition before the hydrolysis reaction or before an enzyme is added to begin the hydrolysis reaction.

With reference again to FIG. 2, in some embodiments, activating the first enzyme 102 comprises heating the first enzyme 102, for example, in the conduit 804 illustrated in FIG. 8. Similarly, in some embodiments, activating the second enzyme 104 comprises heating the second enzyme 104, for example, in the conduit 804 illustrated in FIG. 8. When two or more enzymes are used, the enzymes can be heated in an order that is suitable for the temperature range over which the enzymes have optimal or acceptable catalytic activity.

In some embodiments, a hydrolysis reaction (e.g., starch hydrolysis reaction 400) occurs at a temperature from about 125° F. (51.67° C.) to about 212° F. (100° C.), from about 140° F. (60° C.) to about 205° F. (96.11° C.), or from about 150° F. (65.56° C.) to about 195° F. (90.56° C.). In some embodiments, a hydrolysis reaction (e.g., fiber hydrolysis reaction 500) occurs at a temperature from about 75° F. (23.89° C.) to about 180° F. (82.22° C.), from about 110° F. (43.33° C.) to about 165° F. (73.89° C.), or from about 140° F. (60° C.) to about 155° F. (68.33° C.). The temperature can vary depending upon the enzyme used.

In some embodiments, it can be desirable to activate the first enzyme 102 (e.g., endo-glucanase or endo-cellulase) at a first activation temperature and then activate the second enzyme 104 (e.g., α-amylase) at a second activation temperature that is higher than the first activation temperature. Accordingly, in some embodiments, a composition comprising the first reagent 108, the second reagent 109, the first enzyme 102, and the second enzyme 104 is heated from a pre-activation temperature to the first activation temperature, and from the first activation temperature to the second activation temperature.

Furthermore, in some embodiments, a first deactivation temperature of the first enzyme 102 is higher than the first activation temperature, and the second deactivation temperature of the second enzyme 104 is higher than the second activation temperature. Additionally, in some embodiments, when the first enzyme 102 is added to a composition comprising the first reagent 108, second reagent 109, third reagent, and/or some combination thereof, the composition is already at the first activation temperature. Similarly, in some embodiments, when the second enzyme 104 is added to a composition comprising the first reagent 108, the second reagent 109, the third reagent, and/or some combination thereof the composition is already at the second activation temperature.

In some embodiments, an enzyme is endo-glucanase.

In some embodiments, an enzyme is endo-cellulase and the deactivation temperature is at least about 180° F. (82.22° C.).

In some embodiments, an enzyme is α-amylase (e.g., a thermophilic α-amylase) and the deactivation temperature is at least about 194° F. (90° C.), or at least about 282° F. (138.89° C.). In some embodiments, the enzyme can be deactivated at a lower temperature (e.g., 194° F. (90° C.)) when the moisture content of a composition comprising the enzyme is higher and can be deactivated at a higher temperature when the moisture content is lower. In some embodiments, the enzyme is deactivated after being subject to the deactivation temperature (e.g., 282° F. (138.89° C.)) for at least about 1, 2, 3, 4, 5, 6, 7, 8, 9, 10, 11, 12, 13, 14, or 15 seconds, or about 1 to 15 seconds, or about 10 to about 15 seconds, or no more than 1 minute. In some embodiments the enzyme is deactivated after being subject to the deactivation temperature (e.g., 194° F. (90° C.)) for no more than about 1 to 20 minutes, or about 10 to 20 minutes, or about 15-20 minutes. The conditions used to obtain deactivation at a given deactivation temperature can vary based on factors including the pH, rate of energy input, moisture content, and residence time.

In some embodiments, if high temperature inactivation is undesirable, deactivating an enzyme (e.g., α-amylase) can comprise adding an acid (e.g., hydrochloric acid or sulfuric acid), to lower the pH of the composition comprising an enzyme. For example, at a pH of 5.0 and 90° C. (194° F.) or at a pH of 3.5-4.0 and 80-85° C. (176-185° F.), α-amylase can be deactivated in about 15 minutes. In some embodiments, the pH can be lowered and the speed of deactivation can be increased. In some embodiments, after deactivating the enzyme, the composition comprising the enzyme is provided with a pH closer to neutral by adding a base or buffering component (e.g., sodium carbonate, calcium carbonate).

In some embodiments, for example, as illustrated in FIGS. 8-11, the first enzyme 102 and/or the second enzyme 104 are activated and deactivated in a conduit 804.

In some embodiments of a method according to the invention, the method provides a product composition 122 that comprises, consists essentially of, or consists of at least a portion of grain (e.g., bran, whole grain, etc.). Furthermore, some embodiments provide hydrolyzed products (e.g., hydrolyzed starch molecules 402 and/or hydrolyzed fiber molecules 502) that have reduced molecular weight relative to the first reagent 108, second reagent 109, third reagent, and/or some combination thereof while remaining the same type of molecule (e.g., starch and/or fiber) as the first reagent 108, second reagent 109, third reagent, and/or some combination thereof.

As another example, in some embodiments, a whole grain comprises the first reagent 108, second reagent 109, third reagent, and/or some combination thereof, and the whole grain maintains whole grain status after hydrolyzing the first reagent 108 and/or hydrolyzing the second reagent 109. Furthermore, in some embodiments, a whole grain maintains its standard of identity as whole grain throughout processing (e.g., hydrolysis, pelletizing, drying, and/or granulating). As an example, in accordance with the American Association of Cereal Chemists (AACC) International, "whole grain" or "standard of identity as whole grain" means that the cereal grain, for example, oat, "consists of the intact, ground cracked or flaked caryopsis, whose principal anatomical components—the starchy endosperm, germ and bran—are present in approximately the same relative proportions as they exist in the intact caryopsis." (See, AACC International's Definition of "Whole Grains," approved in 1999, available at http://www.aaccnet.org/initiatives/definitions/pages/wholegrain.aspx (last accessed Feb. 11, 2016).) Further, if the principal nutrients (i.e., starch, fat, protein, dietary fiber, beta-glucan, and sugar) are present in approximately the same relative proportions for a partially hydrolyzed grain and the original grain, it can be assumed that the processed grain (e.g., the partially hydrolyzed grain) maintains its whole grain status. However, since the average molecular weight of starch (e.g., amylopectin) in whole grains varies widely across the various types of whole grains (e.g., 1-400 million Dalton) and even among whole grain oat products, a shift in starch moieties from higher molecular weight to lower molecular weight does not alter whole grain status if the total starch content remains the same. Accordingly, in some embodiments, a composition comprising the first reagent 108, the second reagent 109 and/or third reagent is a whole grain composition comprising caryopses. For example, in some embodiments, the whole grain can comprise the first reagent 108, the second reagent 109, third reagent, and/or some combination thereof (e.g., fiber, starch, protein, and/or some combination thereof). Additionally, in some embodiments, the principal anatomical components of the caryopses (i.e., the starchy endosperm, germ, and bran) are present in the same relative mass ratios both before and after hydrolyzing the first reagent 108, hydrolyzing the second reagent 109, hydrolyzing the third reagent, and/or some combination thereof. Also, in some embodiments, the principal anatomical components of the caryopses are present in the same relative mass ratios in the caryopses both after harvesting when the caryopses are intact and after hydrolyzing the first reagent 108, hydrolyzing the second reagent 109, hydrolyzing the third reagent, and/or some combination thereof in the caryopses.

Further, in some embodiments, if the principal nutrients (i.e., starch, fat, protein, dietary fiber, beta-glucan, and sugar) are present in approximately the same relative proportions for a composition comprising grain before and after hydrolyzing the grain, it can be said that the processed grain maintains its whole grain status. As an illustration, the processed grain can be hydrolyzed grain, for example, grain in which the first reagent 108, the second reagent 109, the third reagent, and/or some combination thereof has been hydrolyzed. Furthermore, since the average molecular weight of starch (e.g., amylopectin) in whole grains varies widely across the various types of whole grains (e.g., 1-400 million Dalton) and even among whole grain oat products, a shift in starch moieties from higher molecular weight to lower molecular weight does not alter whole grain status if the total starch content remains the same or substantially the same (e.g., within +/−10, 9, 8, 7, 6, 5, 4, 3, 2, or 1 wt. % on a dry-total-weight basis). Likewise, since the average molecular weight of fiber in whole grains varies widely across the various types of whole grains and even among whole grain oat products, a shift in fiber moieties from higher molecular weight to lower molecular weight does not alter whole grain status if the total fiber content remains the same or substantially the same (e.g., within +/−10, 9, 8, 7, 6, 5, 4, 3, 2, or 1 wt. % on a dry-total-weight basis). Similarly, since the average molecular weight of protein in whole grains varies widely across the various types of whole grains and even among whole grain oat products, a shift in protein moieties from higher molecular weight to lower molecular weight does not alter whole grain status if the total protein content remains the same or substantially the same (e.g., within +/−10, 9, 8, 7, 6, 5, 4, 3, 2, or 1 wt. % on a dry-total-weight basis).

Additionally, even in a selected variety of grain, variations occur in relative mass ratios of the principal nutrients in grain (i.e., starch, fat, protein, dietary fiber, beta-glucan, and sugar). Accordingly, in some embodiments, the change in relative mass ratios of the principal nutrients due to hydrolyzing the first reagent 108, hydrolyzing the second reagent 109, hydrolyzing the third reagent, other processing, and/or some combination thereof is small enough that the relative mass ratios are still within the natural ranges for the variety of grain, thereby maintaining whole grain status. As used herein, the term mass ratio of X to Y means the mass of X divided by the mass of Y. As an example, if starch is present in a composition at 2 wt. % and protein is present at 1 wt. %, then the mass ratio of starch to protein is 2.

Furthermore, in some embodiments, while hydrolyzing the first reagent 108, hydrolyzing the second reagent 109, hydrolyzing the third reagent, and/or some combination thereof the changes in weight percentages of the starch, fat, protein, dietary fiber, beta-glucan, and sugar in a composition comprising the first reagent 108, the second reagent 109, the third reagent, and/or some combination thereof are no more than about +/−10, 5, 4, 3, 2, or 1 wt. % on a total-dry-weight-basis (e.g., excluding water).

In some embodiments, a bran composition comprises the first reagent 108, second reagent 109, third reagent, and/or some combination thereof. For example, according to the AACCI, "Oat Bran is the food which is produced by grinding clean oat groats or rolled oats and separating the resulting oat flour by sieving bolting, and/or other suitable means into fractions such that the oat bran fraction is not more than 50% of the original starting material and has a total betaglucan content of at least 5.5% (dry-weight basis) and a total dietary fiber content of at least 16.0% (dry-weight basis), and such that at least one-third of the total dietary fiber is soluble fiber."

In some embodiments, a bran composition comprises the first reagent 108, second reagent 109, third reagent, and/or some combination thereof, and no more than about 10, 9, 8, 7, 6, 5, 4, 3, 2, or 1 wt. % of beta-glucan in the bran composition is hydrolyzed to non-beta-glucan molecules (e.g., molecules selected from the group consisting of monosaccharides, disaccharides, and both monosaccharides and disaccharides). In some embodiments, the bran composition comprising the first reagent 108, second reagent 109, third reagent, and/or some combination thereof is oat bran. Additionally, in some embodiments, the product composition 122 is oat bran. Furthermore, in some embodiments the oat bran comprises at least about 5.5 wt. % beta-glucan on a total dry weight basis (e.g., excluding water) and at least about 16.0 wt. % dietary fiber on a total dry weight basis. Also, in some embodiments, at least one-third of the total dietary fiber is soluble fiber.

One embodiment of the invention will now be described with references to FIGS. 8-11 which each illustrate an apparatus comprising a hydrolysis reactor 133, for example, as depicted in FIG. 1. As with the other figures herein, FIGS. 8-11 are illustrative and the features and elements described herein can be omitted, combined, re-ordered, re-arranged, and interchanged as appropriate.

In some embodiments, the hydrolysis reactor 133 comprises a first hydrolysis reaction zone 1202 and a first deactivation zone 1204, for example, as illustrated in FIG. 12 and FIG. 13. In some embodiments a hydrolysis reactor 133 comprises a plurality of hydrolysis reaction zones (e.g., first hydrolysis reaction zone 1202, second hydrolysis reaction zone 1302, third hydrolysis reaction) and/or a plurality of deactivation zones (e.g. first deactivation zone 1204, second deactivation zone 1304, third deactivation zone). In some embodiments the first hydrolysis reaction zone 1202 and the second hydrolysis reaction zone 1302 overlap because at least some portion of the first hydrolysis reaction and at least some portion of the second hydrolysis reaction occur simultaneously. Similarly, in some embodiments the first deactivation zone 1204 and the second deactivation zone 1304 overlap because the first enzyme 102 and the second enzyme 104 are deactivated simultaneously to some extent.

As illustrated in FIG. 12, in some embodiments, a feed 1206 to the first hydrolysis reaction zone 1202 comprises a first reagent 108, as illustrated for example in FIG. 8. In the first hydrolysis reaction zone 1202, the first hydrolysis reaction is catalyzed by a first enzyme 102. As the first hydrolysis reaction progresses, the first reagent 108 reacts with water 106 to form a first hydrolysate intermediate composition 1208. The first hydrolysate intermediate composition 1208 proceeds to a deactivation zone where the first enzyme 102 is deactivated to provide a first hydrolyzed product 1210.

As illustrated in FIG. 13, in some embodiments, a feed 1306 to the second hydrolysis reaction zone 1302 comprises a second reagent 109. In the second hydrolysis reaction zone 1302, the second hydrolysis reaction is catalyzed by a second enzyme 104. As the second hydrolysis reaction progresses, the second reagent 109 reacts with water 106 to form a second hydrolysate intermediate composition 1308. The second hydrolysate intermediate composition 1308 proceeds to a deactivation zone where the second enzyme 104 is deactivated to provide a second hydrolyzed product 1310.

In some embodiments, the preconditioned mixture 111 (depicted, for example in FIG. 1) is the feed to the first hydrolysis reaction zone 1202, the feed to the second hydrolysis reaction zone 1302, the feed to a third hydrolysis reaction zone, and/or some combination thereof. For example, in some embodiments, the preconditioned mixture 111 comprises the first reagent 108, second reagent 109, third reagent, and/or some combination thereof.

As another example, in some embodiments, the preconditioned mixture 111 is the feed 1206 to the first hydrolysis reaction zone 1202, and the first hydrolysate intermediate composition 1208 or the first hydrolyzed product 1210 is the feed 1306 to the second hydrolysis reaction zone 1302. Furthermore, the second hydrolyzed product 1310 can be the feed to a third hydrolysis reaction zone.

As a further example, in some embodiments, the hydrolyzed product comprises the first hydrolyzed product 1210, the second hydrolyzed product 1310, the third hydrolyzed product, and/or some combination thereof.

With reference to FIG. 11, one embodiment of the invention provides a hydrolysis reactor 133 comprising a conduit 804, a composition inlet 808 in the conduit 804, a first enzyme inlet 806 in the conduit 804 downstream of the composition inlet 808, and a deactivating mechanism downstream of the first enzyme inlet 806.

For example, in some embodiments, the conduit 804 is a pipe, tube, or duct. Furthermore, in some embodiments, the deactivating mechanism comprises a deactivating heater 132 or a deactivating fluid inlet 904 in the conduit 804.

In some embodiments, the composition inlet 808 is for a composition comprising starch (e.g., starch molecules 402) and/or fiber (e.g., fiber molecules 502). Additionally, in some embodiments, the composition inlet 808 is in fluid communication with a source 1004 for the composition (e.g., tank provided with a sufficient static head of the composition or a pump).

With reference to FIGS. 10-11, in some embodiments, the hydrolysis reactor 133 comprises an intermediate heater 1006 along the conduit 804, downstream of the composition inlet 808, and upstream of the deactivating fluid inlet 904. For example, the intermediate heater 1006 can be a jacket for gradually heating the composition as the composition flows through the pipe adjacent to the intermediate heater 1006. The intermediate heater 1006 can also be an infrared device, a microwave device, an ultrasonic device, or a heat exchanger.

With reference to FIG. 11, in some embodiments, the hydrolysis reactor 133 comprises a preconditioning fluid inlet 1104 in the conduit 804 downstream of the composition inlet 808. For example, the preconditioning fluid inlet 1104 can comprise a distributor, a nozzle, or a plurality of nozzles.

In some embodiments, the preconditioning fluid 1102 preconditions the composition to provide the composition with a desired water content and desired wet-mix temperature. For example, the desired water content can be set to provide a sufficient number of chemically unbound and/or sterically unhindered water molecules to provide at least a minimum hydrolysis reaction rate. In some embodiments, the composition comprises at least about 50, 60, 70, 80, or 90 wt. % water 106.

In some embodiments, the wet-mix temperature is the temperature of a mixture (e.g., an enzyme, water 106, and at least one material comprising hydrolyzed starch and/or hydrolyzed fiber) fed to a hydrolysis reactor 133. For example, this can be a temperature provided by the preconditioner 129. In some embodiments, the wet mix temperature is at least a temperature sufficient to gelatinize starch in the mixture fed to the hydrolysis reactor. For example, in some embodiments, the wet mix temperature is at least 140° F. (60° C.).

In some embodiments, the preconditioning fluid 1102 is preconditioning steam and/or liquid water, which can also be heated. Accordingly, in some embodiments, the preconditioning fluid inlet 1104 is a preconditioning steam inlet and/or preconditioning hot water 106 inlet.

With reference again to FIG. 11, in some embodiments, the first enzyme inlet 806 is downstream of the composition inlet 808 and the preconditioning fluid inlet 1104. In some embodiments, the hydrolysis reactor 133 comprises a second enzyme inlet 1008 in the conduit 804 downstream of the first enzyme inlet 806. Furthermore, in some embodiments, the deactivating mechanism is downstream of the first enzyme inlet 806 and a second enzyme inlet 1008.

Although various steps (e.g., hydrolyzing, adding, activating, deactivating) are discussed herein with respect to the first enzyme 102, in additional embodiments, the same steps are applicable to the second enzyme 104, the third enzyme or any additional enzymes, as a skilled person would understand after reading this disclosure. Accordingly, additional embodiments can be formed by substituting "second" or "third" for "first", for example, with respect to the first enzyme, first reagent, first deactivating mechanism, etc. Moreover, additional embodiments can be formed by adding second and/or third elements (e.g., a second or third enzyme, reagent, deactivating mechanism, etc.) to the first element described herein (e.g., first enzyme, first reagent, first deactivating mechanism, etc.).

Similarly, although an enzyme (e.g., the first enzyme 102, the second enzyme 104, third enzyme) are discussed herein, in some embodiments, a catalyst can be used in place of the enzyme. Furthermore, in some embodiments the first enzyme 102 and the second enzyme 104 are added to a composition comprising the first reagent 108 and the second reagent 109 at the same time. However, in other embodiments, the second enzyme 104 is added to the composition after the first enzyme 102.

Also, while whole grain, whole pulse, bran, or other more specific terms are used herein, after reading the present disclosure, a skilled person would understand that the more specific terms can generally be replaced with broader terms, namely, at least a portion of a grain and/or at least a portion of a pulse, thereby forming additional embodiments.

Additional Embodiments

The following clauses are offered as further description of the disclosed invention:

1. A method comprising:
    hydrolyzing a first reagent (e.g., fiber molecules or starch molecules) in a first hydrolysis reaction (e.g., fiber hydrolysis reaction or starch hydrolysis reaction); and
    deactivating a first enzyme catalyzing the first hydrolysis reaction (e.g., to produce a first hydrolyzed product with a first target percent conversion);
    wherein the deactivating step lasts no more than about 10 seconds, 5 seconds, 4 seconds, 3 seconds, 2 seconds, or 1 second.
2. The method of any of clauses 1-13 and 22-33, excepting the present clause:
    wherein the first reagent is selected from the group consisting of starch molecules, fiber molecules, and protein molecules.
3. The method of any of clauses 1-13 and 22-33, excepting the present clause:
    wherein the first hydrolysis reaction is a first enzyme-catalyzed hydrolysis reaction selected from the group consisting of a starch-hydrolysis reaction, a fiber-hydrolysis reaction, and a protein-hydrolysis reaction.
4. The method of any of clauses 1-13 and 22-33, excepting the present clause:
    wherein the first hydrolysis reaction is part of a continuous hydrolysis process;
    wherein the first enzyme and a composition comprising the first reagent (e.g., an enzyme-reagent mixture or preconditioned mixture) are fed (e.g., continuously) to a first hydrolysis reaction zone (e.g., a first-enzyme-catalyzed-hydrolysis reaction zone);
    wherein the first enzyme is deactivated (e.g., continuously) in a first deactivation zone; and
    wherein the first deactivation zone begins downstream of where the first hydrolysis reaction zone begins.
5. The method of any of clauses 1-13 and 22-33, excepting the present clause, further comprising:
    deactivating the first enzyme before more than about 10, 9, 8, 7, 6, 5, 4, 3, 2, or 1 wt % of the first reagent has been converted to molecules selected from the group consisting of monosaccharides, disaccharides, and both monosaccharides and disaccharides;
    wherein the first reagent is selected from the group consisting of fiber and starch.
6. The method of any of clauses 1-13 and 22-33, excepting the present clause and clause 12, further comprising:
    hydrolyzing a second reagent in a second hydrolysis reaction catalyzed by a second enzyme, wherein the second reagent is starch;
    deactivating the second enzyme before more than about 10, 9, 8, 7, 6, 5, 4, 3, 2, or 1 wt % of the second reagent has been converted to non-starch molecules (e.g., molecules selected from the group consisting of monosaccharides, disaccharides, and both monosaccharides and disaccharides);
    wherein the first reagent is selected from the group consisting of fiber and protein.
7. The method of any of clauses 1-13 and 22-33, excepting the present clause, further comprising:
    activating the first enzyme by heating the first enzyme (e.g., in a conduit, and/or by adding the first enzyme to a heated first reagent or adding the first enzyme to the first reagent and heating both the first enzyme and the first reagent).
8. The method of any of clauses 1-13 and 22-33, excepting the present clause, further comprising:
    activating a second enzyme (e.g., in a conduit); and
    deactivating the second enzyme (e.g., in a conduit).
9. The method of any of clauses 1-13 and 22-33, excepting the present clause and clause 12, further comprising:
    wherein the first reagent is fiber; and
    wherein a second reagent is starch.
10. The method of any of clauses 1-13 and 22-33, excepting the present clause and clause 26:
    wherein whole grain comprises the first reagent; and
    wherein, after hydrolyzing the first reagent, the whole grain has a mass ratio selected from the group consisting of:
        a mass ratio of fiber to protein equal, within a tolerance of +/−20% (optionally, 15%, 10%, 5%, 4%, 3%, 2% or 1%), to a mass ratio of fiber to protein of the whole grain before hydrolyzing the first reagent;
        a mass ratio of fat to protein equal, within a tolerance of +/−20% (optionally, 15%, 10%, 5%, 4%, 3%, 2% or 1%), to a mass ratio of fat to protein of the whole grain before hydrolyzing the first reagent;
        a mass ratio of starch to protein equal, within a tolerance of +/−20% (optionally, 15%, 10%, 5%, 4%, 3%, 2% or 1%), to a mass ratio of starch to protein of the whole grain before hydrolyzing the first reagent; and
        any combination thereof.
11. The method of any of clauses 1-13 and 22-33, excepting the present clause:
    wherein a bran composition comprises the first reagent; and
    wherein no more than about 10, 9, 8, 7, 6, 5, 4, 3, 2, or 1 wt % of beta-glucan in the bran composition is hydrolyzed to non-beta-glucan molecules (e.g., molecules selected from the group consisting of monosaccharides, disaccharides, and both monosaccharides and disaccharides).

12. The method of any of clauses 1-13 and 22-33, excepting the present clause and clauses 6, 9, 26, and 28-29, further comprising:
providing a composition to a conduit, wherein the composition comprises at least 50 wt. % water, wherein the composition comprises grain with whole grain status, wherein the grain comprises the first reagent, and wherein the first reagent is starch;
mixing the first enzyme with the composition in the conduit to catalyze the first hydrolysis reaction, wherein the first enzyme is α-amylase; and
combining steam with the composition in the conduit to deactivate the first enzyme, thereby maintaining the whole grain status of the grain and thereby providing a product composition, wherein the product composition is food grade.

13. The method of any of clauses 1-13 and 22-33, excepting the present clause, further comprising:
hydrolyzing a second reagent in a second hydrolysis reaction;
deactivating a second enzyme catalyzing the second hydrolysis reaction;
hydrolyzing a third reagent in a third hydrolysis reaction; and
deactivating a third enzyme catalyzing the third hydrolysis reaction.

14. A hydrolysis reactor comprising:
a conduit (e.g., pipe, tube, duct);
a composition inlet in the conduit for a composition (e.g., comprising starch molecules, fiber molecules, protein molecules, or any combination thereof), optionally, wherein the inlet is in fluid communication with a source (e.g., tank with static head, or tank and pump) for the composition;
a first enzyme inlet in the conduit downstream of the composition inlet (and optionally, a preconditioning fluid inlet, for example, a preconditioning steam inlet); and
a first deactivating mechanism (e.g., first deactivating fluid inlet in the conduit) downstream of the first enzyme inlet (and optionally a second enzyme inlet) to deactivate the first enzyme (and/or the second enzyme).

15. The hydrolysis reactor of any of clauses 14-21, excepting the present clause, further comprising:
a preconditioning fluid inlet (e.g., distributor, nozzle, or plurality of nozzles) in the conduit downstream of the composition inlet.

16. The hydrolysis reactor of any of clauses 14-21, excepting the present clause, further comprising:
an intermediate heater along the conduit, downstream of the composition inlet, and upstream of the first deactivating mechanism (e.g., deactivating fluid inlet or deactivating heater).

17. The hydrolysis reactor of any of clauses 14-21, excepting the present clause, further comprising:
an intermediate heating device along the conduit, downstream of the composition inlet, and upstream of the first deactivating mechanism (e.g., deactivating fluid inlet or deactivating heater).

18. The hydrolysis reactor of any of clauses 14-21, excepting the present clause, wherein the hydrolysis reactor is located on a mobile skid.

19. The hydrolysis reactor of any of clauses 14-21, excepting the present clause, further comprising:
a second enzyme inlet in the conduit downstream of the first enzyme inlet;
(and optionally, wherein the second enzyme inlet is downstream of a third enzyme inlet in the conduit).

20. The hydrolysis reactor of any of clauses 14-21, excepting the present clause, further comprising:
a second deactivating mechanism (e.g., second deactivating fluid inlet in the conduit) downstream of the second enzyme inlet to deactivate the second enzyme (and optionally to deactivate a third enzyme).

21. The hydrolysis reactor of any of clauses 14-21, excepting the present clause, further comprising:
a third deactivating mechanism (e.g., third deactivating fluid inlet in the conduit) downstream of a third enzyme inlet to deactivate a third enzyme.

22. A method comprising:
hydrolyzing a first reagent in a first hydrolysis reaction; and
deactivating a first enzyme catalyzing the first hydrolysis reaction;
wherein the deactivating step comprises adding a deactivating fluid, for example, a hot fluid, a liquid (e.g., water, milk, juice, oil, or melted butter), or a gas (e.g., steam) to a composition comprising the first enzyme.

23. A method comprising:
hydrolyzing a first reagent in a first hydrolysis reaction; and
deactivating a first enzyme catalyzing the first hydrolysis reaction;
wherein the deactivating step comprises heating the first enzyme using a deactivating mechanism (for example, mixing a hot fluid with the enzyme or using a deactivating heater (e.g., an infrared device, a microwave device, an ultrasonic device, or a heat exchanger)).

24. A method comprising:
hydrolyzing a first reagent in a first hydrolysis reaction; and
deactivating a first enzyme catalyzing the first hydrolysis reaction;
wherein the hydrolyzing the first reagent and the deactivating the first enzyme occur in a conduit.

25. A method comprising:
hydrolyzing a first reagent in a first hydrolysis reaction; and
deactivating a first enzyme catalyzing the first hydrolysis reaction;
wherein the first hydrolysis reaction occurs in a composition that is at least 50 wt. % water.

26. The method of any of clauses 1-13 and 22-33, excepting the present clause and clauses 10 and 12:
wherein pulse (e.g., whole pulse) comprises the first reagent; and
wherein, after hydrolyzing the first reagent, the whole pulse has a mass ratio selected from the group consisting of:
a mass ratio of fiber to protein equal, within a tolerance of +/−20% (optionally, 15%, 10%, 5%, 4%, 3%, 2% or 1%), to a mass ratio of fiber to protein of the whole pulse before hydrolyzing the first reagent;
a mass ratio of fat to protein equal, within a tolerance of +/−20% (optionally, 15%, 10%, 5%, 4%, 3%, 2% or 1%), to a mass ratio of fat to protein of the whole pulse before hydrolyzing the first reagent;
a mass ratio of starch to protein equal, within a tolerance of +/−20% (optionally, 15%, 10%, 5%, 4%, 3%, 2% or 1%), to a mass ratio of starch to protein of the whole pulse before hydrolyzing the first reagent; and
any combination thereof.

27. The method of any of clauses 1-13 and 22-33, excepting the present clause:
further comprising hydrolyzing at least a portion of at least one material to provide hydrolyzed material;

wherein the at least one material is selected from the group consisting of at least a portion of a pulse (e.g., whole pulse, etc.), at least a portion of a grain (e.g., whole grain, bran, etc.), and any combination thereof;
wherein the at least one material comprises the first reagent;
wherein hydrolyzing the first reagent in the at least one material provides a first hydrolyzed product in the hydrolyzed material;
wherein the first hydrolyzed product is selected from the group consisting of hydrolyzed starch, hydrolyzed fiber, hydrolyzed protein, and any combination thereof; and
wherein the hydrolyzed material has a mass ratio selected from the group consisting of:
a mass ratio of fiber to protein equal, within a tolerance of +/−20% (optionally, 15%, 10%, 5%, 4%, 3%, 2% or 1%), to a mass ratio of fiber to protein of the at least one material;
a mass ratio of fat to protein equal, within a tolerance of +/−20% (optionally, 15%, 10%, 5%, 4%, 3%, 2% or 1%), to a mass ratio of fat to protein of the at least one material;
a mass ratio of starch to protein equal, within a tolerance of +/−20% (optionally, 15%, 10%, 5%, 4%, 3%, 2% or 1%), to a mass ratio of starch to protein of the at least one material; and
any combination thereof.

28. The method of any of clauses 1-13 and 22-33, excepting the present clause and clause 12:
wherein the first enzyme is an endo-cellulase; and
wherein the first enzyme provides about 30-200, about 100-130, or about 115 International Units (IU) of enzyme activity per gram of fiber.

29. The method of clause 6:
wherein the second enzyme is α-amylase; and
wherein the second enzyme provides about 600-3100, about 1700-2000, or about 1,850 Modified Wohlgemuth Units (MWU) of enzyme activity per gram of starch.

30. The method of clause 6:
wherein whole grain comprises the second reagent; and
wherein, after hydrolyzing the second reagent, the whole grain has a mass ratio selected from the group consisting of:
a mass ratio of fiber to protein equal, within a tolerance of +/−20% (optionally, 15%, 10%, 5%, 4%, 3%, 2% or 1%), to a mass ratio of fiber to protein of the whole grain before hydrolyzing the second reagent;
a mass ratio of fat to protein equal, within a tolerance of +/−20% (optionally, 15%, 10%, 5%, 4%, 3%, 2% or 1%), to a mass ratio of fat to protein of the whole grain before hydrolyzing the second reagent;
a mass ratio of starch to protein equal, within a tolerance of +/−20% (optionally, 15%, 10%, 5%, 4%, 3%, 2% or 1%), to a mass ratio of starch to protein of the whole grain before hydrolyzing the second reagent; and any combination thereof.

31. The method of any of clauses 1-13 and 22-33, excepting the present clause:
wherein whole grain comprises the first reagent; and
wherein the whole grain maintains whole grain status after hydrolyzing the first reagent.

32. The method of clause 11:
wherein the bran composition is oat bran; and
wherein the bran composition comprises:
at least about 5.5 wt. % beta-glucan on a total dry weight basis;
at least about 16.0 wt. % dietary fiber on a total dry weight basis; and
wherein at least one-third of the total dietary fiber is soluble fiber.

33. The method of any of clauses 1-13 and 22-33, excepting the present clause, wherein the method provides a product composition; and
wherein the product composition is a food grade product composition.

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of using a hydrolysis reactor, the hydrolysis reactor comprising:
a conduit;
a composition inlet in the conduit for a composition comprising starch;
an α-amylase inlet in the conduit downstream of the composition inlet, wherein the α-amylase inlet provides a path of fluid communication between the conduit and a source for an α-amylase composition, wherein the α-amylase composition comprises α-amylase, wherein the α-amylase catalyzes hydrolysis of the starch in the composition; and
an α-amylase-deactivating mechanism in the conduit, wherein the α-amylase-deactivating mechanism is downstream of the α-amylase inlet, and wherein the α-amylase-deactivating mechanism comprises an α-amylase-deactivating fluid inlet configured to add an α-amylase-deactivating fluid to the composition and thereby deactivate the α-amylase;
wherein the method comprises:
introducing the composition into the conduit through the composition inlet;
introducing the α-amylase into the conduit through the α-amylase inlet;
using the α-amylase to hydrolyze the starch in the composition while the composition is in the conduit;
introducing the α-amylase-deactivating fluid into the conduit through the α-amylase-deactivating fluid inlet;
using the α-amylase-deactivating fluid introduced into the conduit to deactivate the α-amylase and to stop the hydrolysis of the starch in the composition so that, on average, a mass of the composition comprising the starch spends no more than 30 seconds subject to the α-amylase-catalyzed hydrolysis of the starch as measured from addition of the α-amylase to the mass until the α-amylase in the mass has been deactivated.

2. The method of claim 1, wherein the hydrolysis reactor comprises:
a preconditioning fluid inlet in the conduit downstream of the composition inlet;
wherein the method comprises introducing a preconditioning fluid into the conduit through the preconditioning fluid inlet, thereby providing a preconditioned mixture for the step of using the α-amylase to hydrolyze the starch in the composition;

wherein the preconditioned mixture comprises 50 to 90 wt. % water; and wherein the preconditioned mixture is at a temperature from 140 to 212° F.

3. The method of claim 1, wherein the hydrolysis reactor is located on a mobile skid;

wherein the method comprises transporting the hydrolysis reactor on the mobile skid.

4. The method of claim 2, wherein the preconditioning fluid is steam.

5. The method of claim 2, wherein the preconditioning fluid inlet is upstream of the α-amylase inlet.

6. The method of claim 2, wherein the preconditioning fluid is selected from the group consisting of steam, hot water, and a combination thereof.

7. The method of claim 1, wherein the α-amylase-deactivating fluid is used to deactivate the α-amylase in no more than 10 seconds.

8. The method of claim 1, wherein the α-amylase in the hydrolysis reactor is deactivated before more than 10 wt. % of the starch has been converted to non-starch molecules.

9. The method of claim 1, wherein the α-amylase in the hydrolysis reactor is deactivated before more than 10 wt. % of the starch has been converted to non-starch molecules selected from the group consisting of monosaccharides, disaccharides, and both monosaccharides and disaccharides.

10. The method of claim 1, wherein the composition comprises whole grain, and the whole grain comprises the starch; and wherein, after the hydrolysis of the starch is completed, the whole grain has a mass ratio of starch to protein equal, within a first specified tolerance, to a reference mass ratio of starch to protein of the whole grain before hydrolyzing the starch, wherein the first specified tolerance is +/−10% of the reference mass ratio of starch to protein.

11. The method of claim 1, wherein the composition comprises whole grain, and the whole grain comprises the starch;

wherein the hydrolysis of the starch in the composition produces a product;

wherein the product has an average molecular weight of starch, wherein the average molecular weight of the starch in the product has been reduced to no more than 60% of an average molecular weight of the starch in the composition.

12. The method of claim 1, wherein the α-amylase-deactivating fluid inlet is an inlet for a hot fluid.

13. The method of claim 1, wherein the α-amylase-deactivating fluid inlet is an inlet for steam.

14. The method of claim 5, wherein, on average, the mass of the composition comprising the starch takes no more than 30 seconds to flow from the α-amylase inlet to a location downstream of the α-amylase-deactivating mechanism where the hydrolysis reactor is configured to complete deactivation of the α-amylase.

15. The method of claim 14, wherein the α-amylase-deactivating fluid is used to deactivate the α-amylase in no more than 10 seconds.

\* \* \* \* \*